(12) United States Patent
Bakos et al.

(10) Patent No.: US 12,062,423 B2
(45) Date of Patent: Aug. 13, 2024

(54) DRUG ADMINISTRATION DEVICES THAT COMMUNICATE WITH SURGICAL HUBS

(71) Applicant: Janssen Pharmaceuticals, Inc., Titusville, NJ (US)

(72) Inventors: Gregory J. Bakos, Mason, OH (US); Jason L. Harris, Lebanon, OH (US); Frederick E. Shelton, IV, Hillsboro, OH (US); James. Fleming, Bethleham, PA (US); Michael Hutchinson, King of Prussia, PA (US); Francesco N. Albertini, Pleasanton, CA (US); Anthony DiUbaldi, Jackson, NJ (US); Steven Vesole, Redwood City, CA (US); Kevin L. Houser, Springboro, OH (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 784 days.

(21) Appl. No.: 17/068,858

(22) Filed: Oct. 13, 2020

(65) Prior Publication Data

US 2021/0350895 A1     Nov. 11, 2021

Related U.S. Application Data

(60) Provisional application No. 63/020,940, filed on May 6, 2020.

(51) Int. Cl.
*G16H 20/17* (2018.01)
*A61M 5/315* (2006.01)
(Continued)

(52) U.S. Cl.
CPC ............ *G16H 20/17* (2018.01); *A61M 5/315* (2013.01); *G16H 10/60* (2018.01); *G16H 30/00* (2018.01);
(Continued)

(58) Field of Classification Search
CPC ........ G16H 20/17; G16H 40/67; G16H 10/60; G16H 30/00; A61M 5/315; A61M 2205/18; A61M 2205/502; A61M 2205/52
(Continued)

(56) References Cited

U.S. PATENT DOCUMENTS 4,946,069 A    8/1990   Fuchs
6,321,942 B1   11/2001  Krampen et al.
(Continued)

FOREIGN PATENT DOCUMENTS

CN   109821109 A    5/2019
EP     3506312 A1   7/2019
WO   2014100658 A1  6/2014

OTHER PUBLICATIONS

"Diet Coke and Mentos Explained," Weebly, dated no later than Mar. 16, 2020, 2 pages (available at <https://dietcoke-and-mentos.weebly.com/>).
(Continued)

*Primary Examiner* — Md Azad

(57) ABSTRACT

In general, drug administration devices that communicate with surgical hubs and methods of using drug administration devices that communicate with surgical hubs are provided. In one aspect, a surgical system is provided that in one embodiment includes a drug administration device configured to administer a drug to a patient during performance of a surgical procedure. The drug administration device includes a first communications interface and a first processor configured to cause the first communications interface to transmit data regarding operation of the drug administration device during the performance of the surgical procedure. The surgical system also includes a surgical hub including a second processor and a second communications interface. The second communications interface is configured to
(Continued)

receive the transmitted data from the first communications interface during the performance of the surgical procedure.

21 Claims, 14 Drawing Sheets

(51) Int. Cl.
*G16H 10/60* (2018.01)
*G16H 30/00* (2018.01)
*G16H 40/67* (2018.01)

(52) U.S. Cl.
CPC .......... *G16H 40/67* (2018.01); *A61M 2205/18* (2013.01); *A61M 2205/502* (2013.01); *A61M 2205/52* (2013.01)

(58) Field of Classification Search
USPC ............................................................ 700/90
See application file for complete search history.

(56) References Cited

U.S. PATENT DOCUMENTS

| | | | |
|---|---|---|---|
| 7,299,949 | B2 | 11/2007 | Greiner-Perth |
| 8,114,345 | B2 | 2/2012 | Dlugos, Jr. et al. |
| 8,585,659 | B2 | 11/2013 | Shay |
| 9,129,054 | B2 | 9/2015 | Nawana et al. |
| 9,314,808 | B2 | 4/2016 | Allsop |
| 9,555,950 | B2 | 1/2017 | Le Maner et al. |
| 10,380,321 | B2 * | 8/2019 | Kamen .................. G16H 40/60 |
| 10,456,534 | B2 | 10/2019 | Reisacher et al. |
| 10,569,071 | B2 | 2/2020 | Harris et al. |
| 11,194,810 | B2 * | 12/2021 | Butler .................. G06F 16/2455 |
| 11,210,611 | B2 * | 12/2021 | Kamen .................. G16H 20/17 |
| 2015/0274344 | A1 | 10/2015 | Sullivan et al. |
| 2015/0297845 | A1 | 10/2015 | Shahaf et al. |
| 2018/0060527 | A1 | 3/2018 | Kalyanpur et al. |
| 2018/0361085 | A1 | 12/2018 | Malhotra et al. |
| 2019/0200844 | A1 | 7/2019 | Shelton, IV et al. |
| 2019/0200981 | A1 | 7/2019 | Harris et al. |
| 2019/0201046 | A1 | 7/2019 | Shelton, IV et al. |
| 2019/0201114 | A1 | 7/2019 | Shelton, IV et al. |
| 2019/0201130 | A1 * | 7/2019 | Shelton, IV ........... G16H 10/60 |
| 2019/0201137 | A1 * | 7/2019 | Shelton, IV ....... A61B 17/1155 |
| 2019/0201140 | A1 | 7/2019 | Yates et al. |
| 2019/0206004 | A1 | 7/2019 | Shelton, IV et al. |
| 2019/0206555 | A1 | 7/2019 | Morgan et al. |
| 2019/0207857 | A1 * | 7/2019 | Shelton, IV ........ H04L 47/2433 |

OTHER PUBLICATIONS

"Dual Component Epoxy Cartridges K-Series Syringe," Adhesive Dispensing Ltd., dated no later than Mar. 21, 2020, 2 pages (available at <https://www.adhesivedispensing.net/Dual_Component_K_Series_Dispensing_s/236.htm>).

"Molecular Sieve vs Silica Gel: What's the Difference?", Multisorb Fixation Group, dated no later than Mar. 24, 2020, 2 pages (available at <https://www.multisorb.com/blog/pharmaceuticals/molecular-sieve-vs-silica-gel-whats-the-difference/>).

"Orbeez® Toys—Add Water to Make Them Grow!", Maya Toys, dated no later than Mar. 24, 2020, 2 pages (available at <https://mayatoys.net/pages/orbeez>).

"Philips Medication Dispenser," Philips Lifeline, dated no later than Mar. 17, 2020, 6 pages (available at <https://www.lifeline.philips.com/pill-dispenser/health-mdp.html>).

"Study Shows High Altitude and Medication May Not Mix," healthNEWS, University of Cincinnati Academic Health Center, Jan. 14, 1999, 1 page (available at <http://healthnews.uc.edu/news/?/153/>).

"The Companion Dual Chamber Reconstitution Syringe," Credence MedSystems, Inc, dated no later than Mar. 18, 2020, 3 pages <available at <https://www.credencemed.com/dual-chamber/>).

"VapourSoft® Technology," Bespak Europe Ltd., dated no later than Mar. 16, 2020, 2 pages (available at <https://bespak.com/products/injection-devices/vapoursoft-technology/>).

Jae Hung Park et al., "Biodegradable Polymers for Microencapsulation of Drugs," Molecules 2005, 10, p. 146-161.

Man Chiu Fung, "Experimental and numerical study of spray characteristics of nasal spray devices," School of Aerospace, Mechanical and Manufacturing Engineering Science, Engineering and Technology Portfolio, RMIT University, Aug. 2013 (179 pages).

Rafi, "14 List of Chemicals That Glow Under Black Light—Application," Jan. 24, 2018, 3 pages (available at <https://azchemistry.com/list-of-chemicals-that-glow-under-black-light>).

International Preliminary Report on Patentability for Intl. Pat. App. No. PCT/IB2021/058422 mailed Nov. 26, 2021. (11 pages).

International Search Report and Written Opinion for Intl. Pat. App. No. PCT/IB2021/058422 mailed Nov. 26, 2021. (14 pages).

* cited by examiner

DRUG ADMINISTRATION DEVICES THAT COMMUNICATE WITH SURGICAL HUBS

CROSS REFERENCE TO RELATED APPLICATIONS

The present application claims priority to U.S. Prov. App. No. 63/020,940 entitled "Drug Administration Devices That Communicate With External Systems And/Or Other Devices" filed May 6, 2020, which is hereby incorporated by reference in its entirety.

FIELD

The present disclosure relates generally to drug administration devices that communicate with surgical hubs and methods of using drug administration devices that communicate with surgical hubs.

BACKGROUND

Pharmaceutical products (including large and small molecule pharmaceuticals, hereinafter "drugs") are administered to patients in a variety of different ways for the treatment of specific medical indications. Regardless of the manner of the administration, care must be taken when administering drugs to avoid adverse effects on the patient. For example, care must be taken not to administer more than a safe amount of the drug to the patient. This requires consideration of the amount of dose given and the time frame over which the dose is delivered, sometimes in relation to previous doses, or doses of other drugs. Moreover, care must be taken not to inadvertently administer an incorrect drug to the patient, or drugs that have degraded due to their age or storage conditions. All of these considerations can be conveyed in guidance associated with the specific drugs or drug combinations. However, this guidance is not always followed correctly, for example due to mistakes, such as human error. This can lead to adverse effects on the patient or result in inappropriate drug administration, for example insufficient or excessive volume of drug being administered for the specific medical indication.

Patients rarely share the same medical characteristics. For example, patients generally have different ages, weights, general states of health, and medical histories. Therefore the same illness tends to affect patients differently. Thus, while guidance supplied with specific drugs may aid a medical practitioner or patient in determining a suitable dosage amount, dosage frequency, and dosage time (dosage regimen) it will not necessarily inform the medical practitioner or patient of the optimum dosage for a particular patient. In order to determine the optimum dosage, the medical practitioner or patient would have to measure some or all possible factors affecting a patient and consider how the different factors interact. This is often impossible, and so medical practitioners or patients have to make a best guess as to the optimum dosage based on information that they have observed about the patient. These best guesses will rarely result in timely administration of an optimum dosage. Moreover, because the best guess is based on data observed by the medical practitioner or patient, there is an undesirable element of subjectivity and possibility of user error when determining or attempting to administer the best guess dosage.

In relation to how a drug is administered to the patient, there are various dosage forms that can be used. For example, these dosage forms may include parenteral, inhalational, oral, ophthalmic, topical, and suppository forms of one or more drugs.

The dosage forms can be administered directly to the patient via a drug administration device. There are a number of different types of drug administration devices commonly available for delivery of the various dosage forms including: syringes, injection devices (e.g., autoinjectors, jet injectors, and infusion pumps), and inhalers.

SUMMARY

In general, drug administration devices that communicate with surgical hubs and methods of using drug administration devices that communicate with surgical hubs are provided.

In one aspect, a surgical system is provided that in one embodiment includes a drug administration device configured to administer a drug to a patient during performance of a surgical procedure. The drug administration device includes a first communications interface and a first processor configured to cause the first communications interface to transmit data regarding operation of the drug administration device during the performance of the surgical procedure. The surgical system also includes a surgical hub including a second processor and a second communications interface. The second communications interface is configured to receive the transmitted data from the first communications interface during the performance of the surgical procedure.

The surgical system can vary in any number of ways. For example, the data regarding operation of the drug administration device during the performance of the surgical procedure can include at least one of image data showing at least a portion of the drug administration device during the performance of the surgical procedure, and data gathered by a sensor of the drug administration device during the performance of the surgical procedure. In at least some embodiments, the data regarding operation of the drug administration device during the performance of the surgical procedure can include at least the image data, a memory of the surgical hub can be configured to store second image data conveying correct administration of the drug administration device, and the second processor can be configured to determine, using the image data and the second image data, whether the drug administration device experienced a failure event during the performance of the surgical procedure. In at least some embodiments, the data regarding operation of the drug administration device during the performance of the surgical procedure can include at least the data gathered by the sensor, and the second processor can be configured to determine, using the data gathered by the sensor, whether the drug administration device experienced a failure event during the performance of the surgical procedure.

For another example, the second processor can be configured to determine, using the received data, whether the drug administration device experienced a failure event during the performance of the surgical procedure. In at least some embodiments, in response to determining that the drug administration device experienced a failure event during the performance of the surgical procedure, the second processor can be configured to cause the second communications interface to transmit an operation instruction to the first communications interface of the drug administration device that instructs the drug administration device to alter its operation.

For yet another example, the surgical system can also include a cloud-based server configured to be remotely located from the drug administration device and from the surgical hub, and the server can include a third communications interface configured to receive data from the second communications interface that the surgical hub received from the drug administration device regarding the operation of the drug administration device during the performance of the surgical procedure. In at least some embodiments of the surgical system also including the cloud-based server, the surgical system can also include a second drug administration device configured to administer a drug to a second patient during performance of a second surgical procedure, the second drug administration device can include a fourth communications interface, the surgical system can also include a second surgical hub including a second processor and a fifth communications interface, the fifth communications interface can be configured to receive data from the fourth communications interface during the performance of the second surgical procedure, the third communications interface can be configured to receive data from the fifth communications interface, the cloud-based server can be configured to be remotely located from the second drug administration device and from the second surgical hub, and the drug administration device and the surgical hub can be configured to be remotely located from the second drug administration device and from the second surgical hub. In at least some embodiments of the surgical system also including the cloud-based server, the cloud-based server can include a third processor configured to cause an electronic medical record (EMR) of the patient to be updated based on the data received from the surgical hub, and in at least some embodiments, the third processor can be configured to, based on the data from the surgical hub and on the EMR of the patient, cause the third communications interface to transmit an alert to the second communications interface of the surgical hub that indicates a critical condition related to the drug. In at least some embodiments of the surgical system also including the cloud-based server, the second communications interface of the surgical hub can be configured to receive image data from the third communications interface of the cloud-based server, the image data can convey correct administration of the drug administration device, and the second processor of the surgical hub can be configured to determine, using the image data and the data that the surgical hub received from the drug administration device, whether the drug administration device experienced a failure event during the performance of the surgical procedure. In at least some embodiments of the surgical system also including the cloud-based server, the cloud-based server can include a memory storing conveying correct administration of the drug administration device, and the cloud-based server can include a third processor configured to determine, using the image data and the data that the cloud-based server received from the surgical hub, whether the drug administration device experienced a failure event during the performance of the surgical procedure.

For still another example, the second communications interface of the surgical hub can be configured to communicate an operation instruction to the first communications interface of the drug administration device that instructs the drug administration device to alter its operation, and the operation instruction can be based on the data the surgical hub received from the drug administration device. For another example, the drug administration device and the surgical hub can each be configured to be located in an operating room in which the surgical procedure is being performed.

In another aspect, a surgical method is provided that in one embodiment includes administering a drug to a patient from a drug administration device during performance of a surgical procedure, and, after the administration of the drug, causing a first communications interface of the drug administration device to transmit data to a second communications interface of a surgical hub regarding operation of the drug administration device during the performance of the surgical procedure. The drug administration device is configured to administer the drug to the patient during performance of the surgical procedure. The drug administration device includes the first communications interface and a first processor configured to cause the first communications interface to transmit data regarding operation of the drug administration device during the performance of the surgical procedure. The surgical hub includes a second processor and the second communications interface. The second communications interface is configured to receive the transmitted data from the first communications interface during the performance of the surgical procedure.

The surgical method can have any number of variations. For example, the surgical method can also include the second processor determining, using the received data, whether the drug administration device experienced a failure event during the performance of the surgical procedure. In at least some embodiments, the surgical method can also include, in response to determining that the drug administration device experienced a failure event during the performance of the surgical procedure, the second processor causing the second communications interface to transmit an operation instruction to the first communications interface of the drug administration device that instructs the drug administration device to alter its operation.

For another example, the surgical method can also include the second processor causing a display of the surgical hub to show information indicative of the received data.

For yet another example, the surgical method can also include the second processor causing the second communications interface to communicate the received data to a cloud-based server. In at least some embodiments, the surgical method can also include the second processor prioritizing the received data before causing the second communications interface to communicate the received data to the cloud-based server.

BRIEF DESCRIPTION OF DRAWINGS

The present invention is described by way of reference to the accompanying figures which are as follows.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Examples of various types of drug administration devices, namely: an autoinjector 100, an infusion pump 200, and an inhaler 300, are described below.

Autoinjectors

Figure 1:
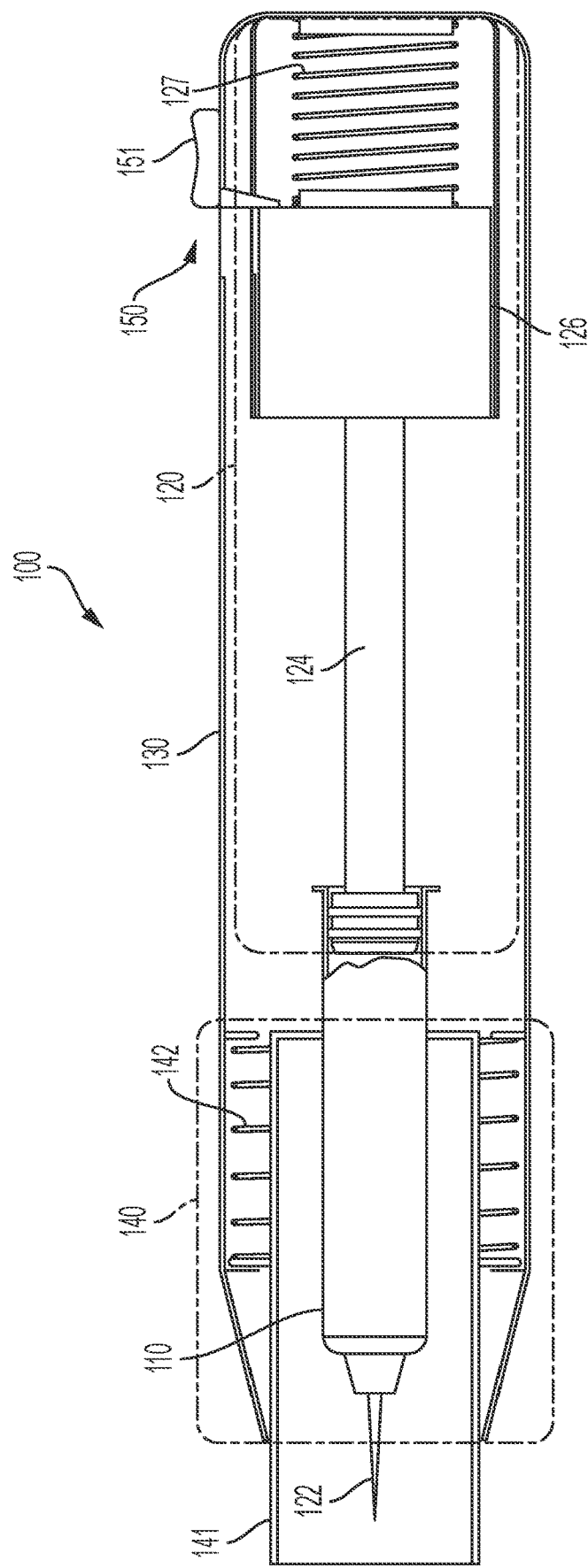
FIG. 1 is a schematic view of one embodiment of a first type of drug administration device, namely an autoinjector.

FIG. 1 is a schematic exemplary view of a first type of drug delivery device (also referred to herein as a "drug administration device"), namely an injection device, in this example an autoinjector 100, useable with embodiments described herein. The autoinjector 100 includes a drug holder 110, which retains a drug to be dispensed, and a dispensing mechanism 120, which is configured to dispense a drug from the drug holder 110 so that it can be administered to a patient. The drug holder 110 is typically in the form of a container which contains the drug, for example it may be provided in the form of a syringe or a vial, or be any other suitable container which can hold the drug. The autoinjector 100 includes a discharge nozzle 122, for example a needle of a syringe, which is provided at a distal end of the drug holder 110. The dispensing mechanism 120 includes a drive element 124, which itself may also include a piston and/or a piston rod, and drive mechanism 126. The dispensing mechanism 120 is located proximal to the end of the drug holder 110 and towards the proximal end of the autoinjector 100.

The autoinjector 100 includes a housing 130 which contains the drug holder 110, the drive element 124, and the drive mechanism 126 within the body of the housing 130, as well as containing the discharge nozzle 122, which, prior to injection, would typically be contained fully within the housing 130, but which would extend out of the housing 130 during an injection sequence to deliver the drug. The dispensing mechanism 120 is arranged so that the drive element 124 is advanced through the drug holder 110 in order to dispense the drug through the discharge nozzle 122, thereby allowing the autoinjector 100 to administer a drug retained in drug holder 110 to a patient. In some instances, a user may advance the drive element 124 through the drug holder 110 manually. In other instances, the drive element 124 may be advanced through the drug holder 110 under control of a robotic surgical system. In other instances, the drive mechanism 126 may include a stored energy source 127 which advances the drive element 124 without user assistance. The stored energy source 127 may include a resilient biasing member such as a spring, or a pressurized gas, or electronically powered motor and/or gearbox.

The autoinjector 100 includes a dispensing mechanism protection mechanism 140. The dispensing mechanism protection mechanism 140 typically has two functions. Firstly, the dispensing mechanism protection mechanism 140 can function to prevent access to the discharge nozzle 122 prior to and after injection. Secondly, the autoinjector 100 can function, such that when put into an activated state, e.g., the dispensing mechanism protection mechanism 140 is moved to an unlocked position, the dispensing mechanism 120 can be activated.

The protection mechanism 140 covers at least a part of the discharge nozzle 122 when the drug holder 110 is in its retracted position proximally within the housing 130. This is to impede contact between the discharge nozzle 122 and a user. Alternatively, or in addition, the protection mechanism 140 is itself configured to retract proximally to expose the discharge nozzle 122 so that it can be brought into contact with a patient. The protection mechanism 140 includes a shield member 141 and return spring 142. The return spring 142 acts to extend the shield member 141 from the housing 130, thereby covering the discharge nozzle 122 when no force is applied to the distal end of the protection mechanism 140. If a user applies a force to the shield member 141 against the action of the return spring 142 to overcome the bias of the return spring 142 (or a robotic surgical system causes such a force to be provided to the shield member 141), the shield member 141 retracts within the housing 130, thereby exposing the discharge nozzle 122. The protection mechanism 140 may alternatively, or in addition, include an extension mechanism (not shown) for extending the discharge nozzle 122 beyond the housing 130, and may further include a retracting mechanism (not shown) for retracting the discharge nozzle 122 within the housing 130. The protection mechanism 140 may alternatively, or in addition, include a housing cap and/or discharge nozzle boot, which can be attached to the autoinjector 100. Removal of the housing cap would typically also remove the discharge nozzle boot from the discharge nozzle 122.

The autoinjector 100 also includes a trigger 150. The trigger 150 includes a trigger button 151 which is located on an external surface of the housing 130 so that it is accessible by a user of the autoinjector 100 and/or by a robotic surgical system configured to control actuation of the trigger 150. When the trigger 150 is pressed by a user (or a robotic surgical system causes the trigger 150 to be pressed), it acts to release the drive mechanism 126 so that, via the drive element 124, the drug is then driven out of the drug holder 110 via the discharge nozzle 122.

The trigger 150 can also cooperate with the shield member 141 in such a way that the trigger 150 is prevented from being activated until the shield member 141 has been retracted proximally sufficiently into the housing 130 into an unlocked position, for example by pushing a distal end of the shield member 141 against the skin of a patient. When this has been done, the trigger 150 becomes unlocked, and the autoinjector 100 is activated such that the trigger 150 can be depressed and the injection and/or drug delivery sequence is then initiated. Alternatively, retraction of the shield member 141 alone in a proximal direction into the housing 130 can act to activate the drive mechanism 126 and initiate the injection and/or drug delivery sequence. In this way, the autoinjector 100 has device operation prevention mechanism which prevents dispensing of the drug by, for example, preventing accidental release of the dispensing mechanism 120 and/or accidental actuation of the trigger 150.

While the foregoing description relates to one example of an autoinjector, this example is presented purely for illustration, the present invention is not limited solely to such an autoinjector. A person skilled in the art understands that various modifications to the described autoinjector can be implemented within the scope of the present disclosure.

Autoinjectors of the present disclosure can be used to administer any of a variety of drugs, such as any of epinephrine, Rebif, Enbrel, Aranesp, atropine, pralidoxime chloride, and diazepam.

Infusion Pumps

Patients can require precise, continuous delivery of medication or medication delivery on a regular or frequent basis at set periodic intervals. Infusion pumps can provide such controlled drug infusion by facilitating the administering of the drug at a precise rate that keeps the drug concentration within a therapeutic margin, without requiring frequent attention by a healthcare professional or the patient.

Figure 2:
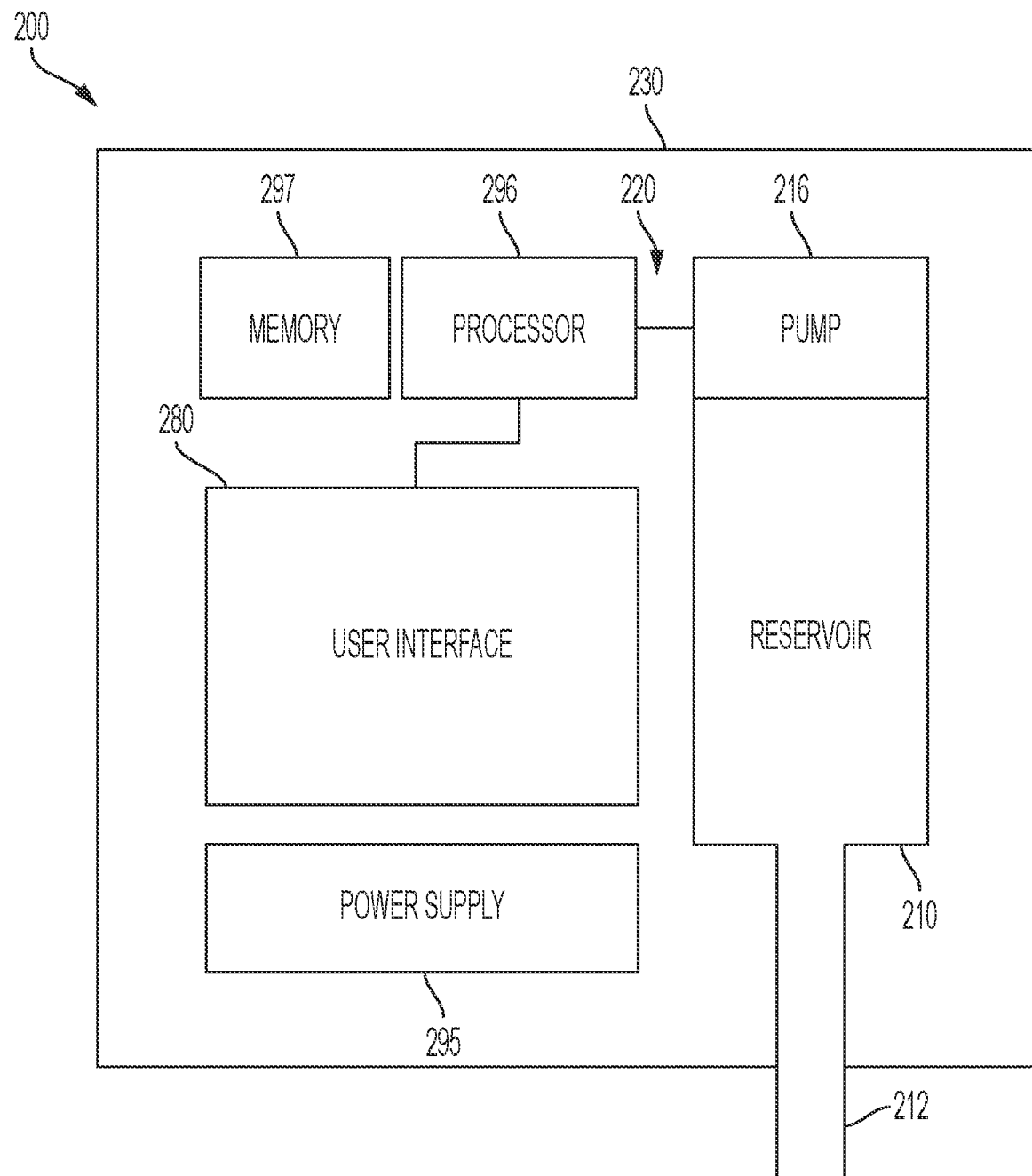
FIG. 2 is a schematic view of one embodiment of a second type of drug administration device, namely an infusion pump.

FIG. 2 is a schematic exemplary view of a second type of drug delivery device, namely an infusion pump 200, useable with the embodiments described herein. The infusion pump 200 includes a drug holder 210 (also referred to herein as a "reservoir") in the form of a reservoir for containing a drug to be delivered, and a dispensing mechanism 220 including a pump 216 configured to dispense a drug contained in the reservoir, so that the drug can be delivered to a patient. These components of the infusion pump 200 are located within a housing 230. The dispensing mechanism 220 further includes an infusion line 212. The drug is delivered from the reservoir 210 upon actuation of the pump 216 via the infusion line 212, which can take the form of a cannula. The pump 216 can take the form of an elastomeric pump, a peristaltic pump, an osmotic pump, or a motor-controlled piston in a syringe. Typically, the drug is delivered intravenously, although subcutaneous, arterial and epidural infusions can also be used.

Infusion pumps of the present disclosure can be used to administer any of a variety of drugs, such as any of insulin, antropine sulfate, avibactam sodium, bendamustine hydrochloride, carboplatin, daptomycin, epinephrine, levetiracetam, oxaliplatin, paclitaxel, pantoprazole sodium, treprostinil, vasopressin, voriconazole, and zoledronic acid.

The infusion pump 200 further includes control circuitry, for example a processor 296 in addition to a memory 297 and a user interface 280, which together provide a triggering mechanism and/or dosage selector for the pump 200. The user interface 280 can be implemented by a display screen located on the housing 230 of the infusion pump 200. The control circuitry and user interface 280 can be located within the housing 230 or external thereto and can communicate via a wired or wireless interface with the pump 216 to control its operation.

Actuation of the pump 216 is controlled by the processor 296, which is in communication with the pump 216 for controlling the pump's operation. The processor 296 can be programmed by a user (e.g., patient or healthcare professional) via a user interface 280 and/or can be programmed electronically using a computer system (e.g., using a robotic surgical system configured to control operation of the pump 216). This enables the infusion pump 200 to deliver the drug to a patient in a controlled manner. The user (or computer system) can enter parameters, such as infusion duration and delivery rate. The delivery rate can be set to a constant infusion rate or as set intervals for periodic delivery, typically within pre-programmed limits. The programmed parameters for controlling the pump 216 are stored in and retrieved from the memory 297 which is in communication with the processor 296. The user interface 280 can take the form of a touch screen or a keypad.

A power supply 295 provides power to the pump 216 and can take the form of an energy source which is integral to the pump 216 and/or a mechanism for connecting the pump 216 to an external source of power.

The infusion pump 200 can take on a variety of different physical forms depending on its designated use. It can be a stationary, non-portable device, e.g., for use at a patient's bedside, in an operating room, etc., or it can be an ambulatory infusion pump which is designed to be portable or wearable. An integral power supply 295 is particularly beneficial for ambulatory infusion pumps.

While the foregoing description relates to one example of an infusion pump, this example is provided purely for illustration. The present disclosure is not limited to such an infusion pump. A person skilled in the art understands that various modifications to the described infusion pump can be implemented within the scope of the present disclosure. For example, the processor may be pre-programmed, such that it is not necessary for the infusion pump to include a user interface.

Inhalers

Figure 3:
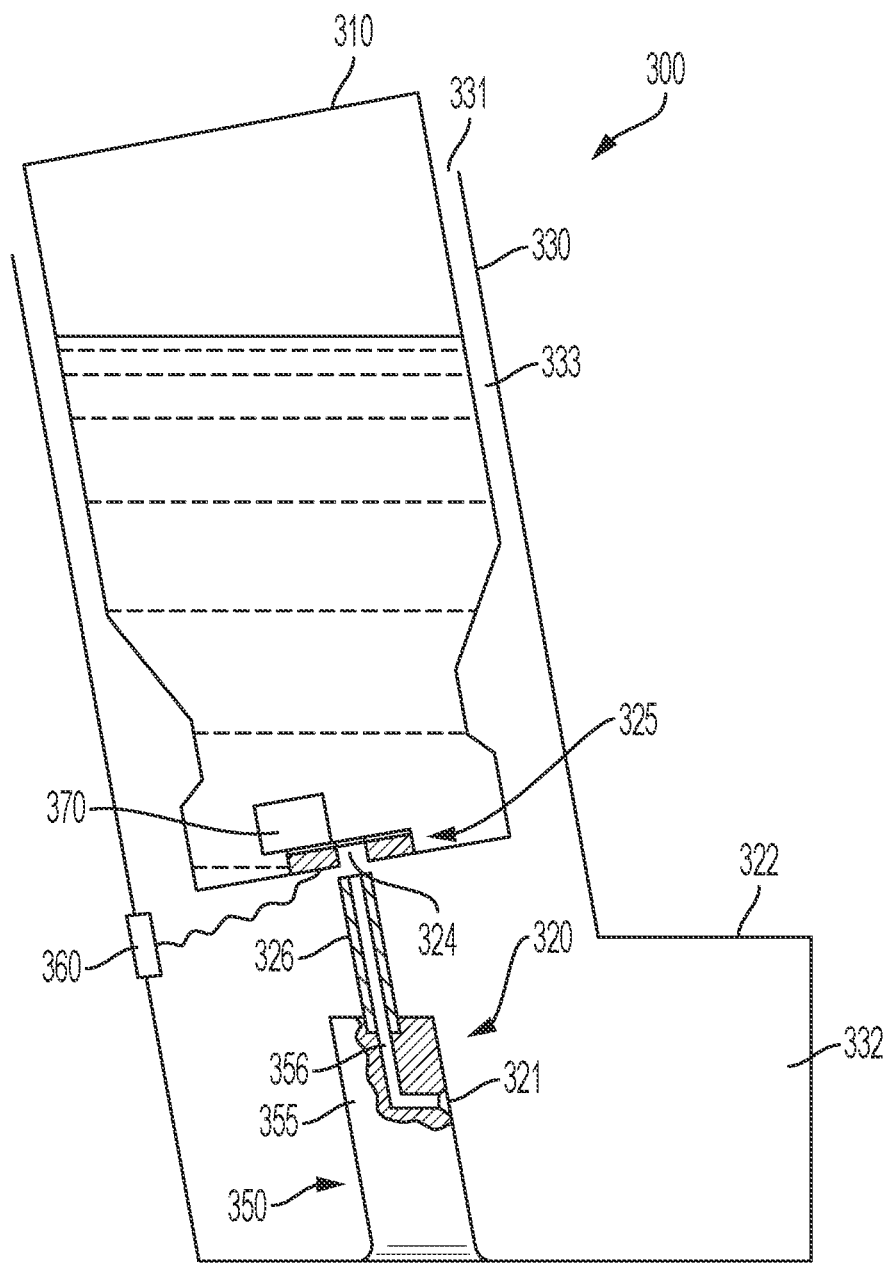
FIG. 3 is a schematic view of one embodiment of a third type of drug administration device, namely an inhaler.
Figure 4:
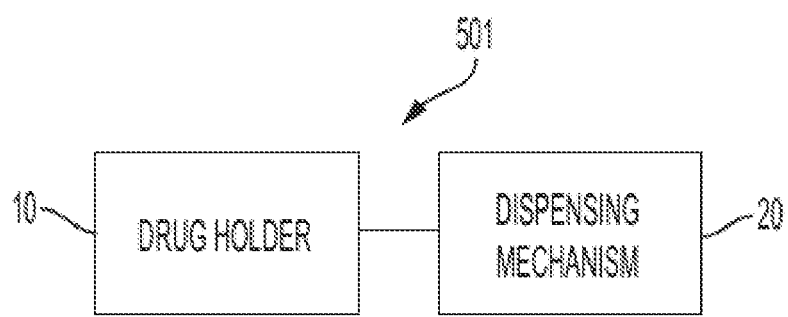
FIG. 4 is a schematic view of a general drug administration device.
Figure 5:
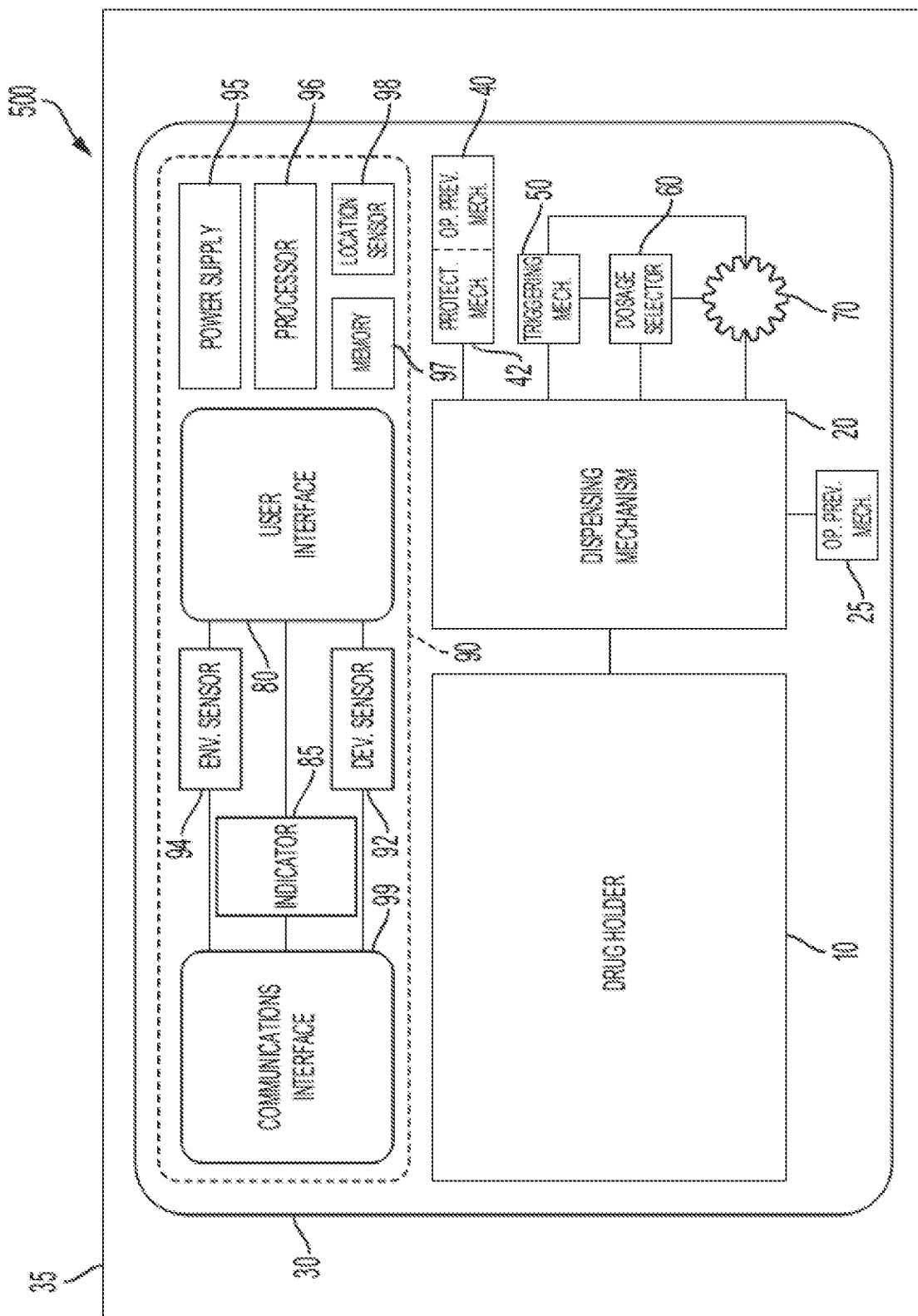
FIG. 5 is a schematic view of a universal drug administration device.

FIG. 3 is a schematic view of a third type of drug administration device, namely an inhaler 300. Inhaler 300 includes a drug holder 310 in the form of a canister. The drug holder 310 contains a drug that would typically be in solution or suspension with a suitable carrier liquid. The inhaler 300 further includes a dispensing mechanism 320, which includes a pressurized gas for pressurizing the drug holder 310, a valve 325 and nozzle 321. The valve 325 forms an outlet of the drug holder 310. The valve 325 includes a narrow opening 324 formed in the drug holder 310 and a movable element 326 that controls the opening 324. When the movable element 326 is in a resting position, the valve 325 is in a closed or unactuated state in which the opening 324 is closed and the drug holder 310 is sealed. When the movable element 326 is actuated from the resting position to an actuated position, the valve 325 is actuated into an open state in which the opening 324 is open. Actuation of the movable element 326 from the resting position to the actuated position comprises moving the movable element 326 into the drug holder 310. The movable element 326 is resiliently biased into the resting position. In the open state of the valve 325, the pressurized gas propels the drug in solution or suspension with the suitable liquid out of the drug holder 310 through the opening 324 at high speed. The high speed passage of the liquid through the narrow opening 324 causes the liquid to be atomized, that is, to transform from a bulk liquid into a mist of fine droplets of liquid and/or into a gas cloud. A patient may inhale the mist of fine droplets and/or the gas cloud into a respiratory passage. Hence, the inhaler 300 is capable of delivering a drug retained within the drug holder 310 into a respiratory passage of a patient.

The drug holder 310 is removably held within a housing 330 of the inhaler 300. A passage 333 formed in the housing 330 connects a first opening 331 in the housing 330 and a second opening 332 in the housing 330. The drug holder 310 is received within the passage 333. The drug holder 310 is slidably insertable through the first opening 331 of the housing 330 into the passage 333. The second opening 332 of the housing 330 forms a mouthpiece 322 configured to be placed in a patient's mouth or a nosepiece configured to be placed in a patient's nostril, or a mask configured to be placed over the patient's mouth and nose. The drug holder 310, the first opening 331 and the passage 333 are sized such that air can flow through the passage 333, around the drug holder 310, between the first opening 331 and the second opening 332. The inhaler 300 can be provided with a dispensing mechanism protection mechanism 140 in the form of a cap (not shown) which can be fitted to the mouthpiece 322.

Inhaler 300 further includes a trigger 350 including a valve actuation feature 355 configured to actuate the valve 325 when the trigger 350 is activated. The valve actuation feature 355 is a projection of the housing 330 into the passage 333. The drug holder 310 is slidably movable within the passage 333 from a first position into a second position. In the first position, an end of the movable element 326 in the resting position abuts the valve actuation feature 355. In the second position, the drug holder 310 can be displaced towards the valve actuation feature 355 such that the valve actuation feature 355 moves the movable element 326 into the drug holder 310 to actuate the valve 325 into the open state. The user's hand (or other element handheld by a user or controlled by a robotic surgical system) provides the necessary force to move the drug holder 310 from the first position to the second position against the resiliently biased movable element 326. The valve actuation feature 355 includes an inlet 356, which is connected to the nozzle 321. The inlet 356 of the valve actuation feature 355 is sized and positioned to couple to the opening 324 of the valve 325 such that the ejected mist of droplets and/or gas cloud can enter the inlet 356 and exit from the nozzle 321 into the passage 333. The nozzle 321 assists in the atomization of the bulk liquid into the mist of droplets and/or gas cloud.

The valve 325 provides a metering mechanism 370. The metering mechanism 370 is configured to close the valve after a measured amount of liquid, and therefore, drug, has passed through the opening 324. This allows a controlled dose to be administered to the patient. Typically, the measured amount of liquid is pre-set, however, the inhaler 300 can be equipped with a dosage selector 360 that is operable by a user and/or electronically by a computer system to change the defined amount of liquid.

While the foregoing description relates to one particular example of an inhaler, this example is purely illustrative. The description should not be seen as limited only to such an inhaler. A person skilled in the art understands that numerous other types of inhalers and nebulizers may be used with the present disclosure. For example, the drug can be in a powdered form, the drug can be in liquid form, or the drug can be atomized by other forms of dispensing mechanism 320 including ultrasonic vibration, compressed gas, a vibrating mesh, or a heat source.

The inhalers of the present disclosure can be used to administer any of a variety of drugs, such as any of mometasone, fluticasone, ciclesonide, budesonide, beclomethasone, vilanterol, salmeterol, formoterol, umeclidinium, glycopyrrolate, tiotropium, aclidinium, indacaterol, salmeterol, and olodaterol.

Drug Administration Devices

As will be appreciated from the foregoing, various components of drug delivery devices are common to all such devices. These components form the essential components of a universal drug administration device. A drug administration device delivers a drug to a patient, where the drug is provided in a defined dosage form within the drug administration device.

FIG. 4 is a generalized schematic view of such a universal drug administration device 501, and FIG. 5 is an exemplary embodiment of such a universal drug administration device 500. Examples of the universal drug administration device 500 include injection devices (e.g., autoinjectors, jet injectors, and infusion pumps), nasal spray devices, and inhalers.

As shown in FIG. 4, the drug administration device 501 includes in general form the features of a drug holder 10 and a dispensing mechanism 20. The drug holder 10 holds a drug in a dosage form to be administered. The dispensing mechanism 20 is configured to release the dosage form from the drug holder 10 so that the drug can be administered to a patient.

FIG. 5 shows a further universal drug administration device 500 which includes a number of additional features. A person skilled in the art understands that these additional features are optional for different embodiments and can be utilized in a variety of different combinations such that the additional features may be present or may be omitted from a given embodiment of a particular drug administration device, depending upon requirements, such as the type of drug, dosage form of the drug, medical indication being treated with the drug, safety requirements, whether the device is powered, whether the device is portable, whether the device is used for self-administration, and many other requirements which will be appreciated by a person skilled in the art. Similar to the universal device of FIG. 4, the drug administration device 500 of FIG. 5 includes a housing 30 which accommodates the drug holder 10 and dispensing mechanism 20.

The device 500 is provided with a triggering mechanism 50 for initiating the release of the drug from the drug holder 10 by the dispensing mechanism 20. The device 500 includes the feature of a metering/dosing mechanism 70 which measures out a set dose to be released from the drug holder 10 via the dispensing mechanism 20. In this manner, the drug administration device 500 can provide a known dose of determined size. The device 500 includes a dosage selector 60 which enables a user to set the dose volume of drug to be measured out by the metering mechanism 50. The dose volume can be set to one specific value of a plurality of predefined discrete dose volumes, or any value of predefined dose volume within a range of dose volumes.

The device 500 includes a device operation prevention mechanism 40 or 25 which when in a locked state will prevent and/or stop the dispensing mechanism 20 from releasing the drug out of the drug holder 10, and when in an unlocked state will permit the dispensing mechanism 20 to release the drug dosage from out of the drug holder 10. This can prevent accidental administration of the drug, for example to prevent dosing at an incorrect time, or for preventing inadvertent actuation. The device 500 also includes a dispensing mechanism protection mechanism 42 which prevents access to at least a part of the dispensing mechanism 20, for example for safety reasons. The device operation prevention mechanism 40 and the dispensing mechanism protection mechanism 42 can be the same component.

The device 500 includes a device indicator 85 which is configured to present information about the status of the drug administration device and/or the drug contained therein. The device indicator 85 can be a visual indicator, such as a display screen, or an audio indicator. The device 500 includes a user interface 80 which can be configured to present a user of the device 500 with information about the device 500 and/or to enable the user to control the device 500. The device 500 includes a device sensor 92 which is configured to sense information relating to the drug administration device and/or the drug contained therein, for example dosage form and device parameters. As an example, in embodiments which include a metering mechanism 70 and a dosage selector 60, the embodiment can further include one or more device sensors 92 configured to sense one or more of: the dose selected by a user using dosage selector 60, the dose metered by the metering mechanism 70 and the dose dispensed by the dispensing mechanism 20. Similarly, an environment sensor 94 is provided which is configured to sense information relating to the environment in which the device 500 is present, such as the temperature of the environment, the humidity of the environment, location, and time. There can be a dedicated location sensor 98 which is configured to determine the geographical location of the device 500, e.g., via satellite position determination, such as GPS. The device 500 also includes a communications interface 99 which can communicate externally data which has been acquired from the various sensors about the device and/or drug.

If required, the device 500 includes a power supply 95 for delivering electrical power to one or more electrical components of the device 500. The power supply 95 can be a source of power which is integral to device 500 and/or a mechanism for connecting device 500 to an external source of power. The drug administration device 500 also includes a computer system 90 including a processor 96 and a memory 97 powered by the power supply 95 and in communication with each other, and optionally with other electrical and control components of the device 500, such as the environment sensor 94, the location sensor 98, the device sensor 92, the communications interface 99, and/or the indicator 85. The processor 96 is configured to obtain data acquired from the environment sensor 94, the device sensor 92, the communications interface 99, the location sensor 98, and/or the user interface 80 and process it to provide data output, for example to indicator 85 and/or to communications interface 99.

In some embodiments, the drug administration device 500 is enclosed in packaging 35. The packaging 35 can further include a combination of a processor 96, a memory 97, a user interface 80, a device indicator 85, a device sensor 92, a location sensor 98, and/or environment sensors 94 as described herein, and these can be located externally on the housing of the device 500.

A person skilled in the art will appreciate that the universal drug administration device 500 including the drug holder 10 and the dispensing mechanism 20 can be provided with a variety of the optional features described above, in a number of different combinations. Moreover, the drug administration device 500 can include more than one drug holder 10, optionally with more than one dispensing mechanism 20, such that each drug holder 10 has its own associated dispensing mechanism 20.

Drug Dosage Forms

Conventionally, drug administration devices utilize a liquid dosage form. It will be appreciated by a person skilled in the art, however, that other dosage forms are available.

One such common dosage form is a tablet. The tablet may be formed from a combination of the drug and an excipient that are compressed together. Other dosage forms are pastes, creams, powders, ear drops, and eye drops.

Further examples of drug dosage forms include dermal patches, drug eluting stents and intrauterine devices. In these examples, the body of the device includes the drug and can be configured to allow the release of the drug under certain circumstances. For example, a dermal patch may include a polymeric composition containing the drug. The polymeric composition allows the drug to diffuse out of the polymeric composition and into skin of a patient. Drug eluting stents and intrauterine devices can operate in an analogous manner. In this way, the patches, stents, and intrauterine devices can themselves be considered drug holders with an associated dispensing mechanism.

Any of these dosage forms can be configured to have the drug release initiated by certain conditions. This can allow the drug to be released at a desired time or location after the dosage form has been introduced into the patient. In particular, the drug release can be initiated by an external stimulus. Moreover, these dosage forms can be contained prior to administration in a housing, which can be in the form of packaging. This housing can contain some of the optional features described above which are utilized with the universal drug administration device 500.

The drug administered by the drug administration devices of the present disclosure can be any substance that causes a change in an organism's physiology or psychology when consumed. Examples of drugs that the drug administration devices of the present disclosure can administer include 5-alpha-reductase inhibitors, 5-aminosalicylates, 5HT3 receptor antagonists, ACE inhibitors with calcium channel blocking agents, ACE inhibitors with thiazides, adamantane antivirals, adrenal cortical steroids, adrenal corticosteroid inhibitors, adrenergic bronchodilators, agents for hypertensive emergencies, agents for pulmonary hypertension, aldosterone receptor antagonists, alkylating agents, allergenics, alpha-glucosidase inhibitors, alternative medicines, amebicides, aminoglycosides, aminopenicillins, aminosalicylates, AMPA receptor antagonists, amylin analogs, analgesic combinations, analgesics, androgens and anabolic steroids, Angiotensin Converting Enzyme Inhibitors, angiotensin II inhibitors with calcium channel blockers, angiotensin II inhibitors with thiazides, angiotensin receptor blockers, angiotensin receptor blockers and neprilysin inhibitors, anorectal preparations, anorexiants, antacids, anthelmintics, anti-angiogenic ophthalmic agents, anti-CTLA-4 monoclonal antibodies, anti-infectives, anti-PD-1 monoclonal antibodies, antiadrenergic agents (central) with thiazides, antiadrenergic agents (peripheral) with thiazides, antiadrenergic agents, centrally acting, antiadrenergic agents, peripherally acting, antiandrogens, antianginal agents, antiarrhythmic agents, antiasthmatic combinations, antibiotics/antineoplastics, anticholinergic antiemetics, anticholinergic antiparkinson agents, anticholinergic bronchodilators, anticholinergic chronotropic agents, anticholinergics/antispasmodics, anticoagulant reversal agents, anticoagulants, anticonvulsants, antidepressants, antidiabetic agents, antidiabetic combinations, antidiarrheals, antidiuretic hormones, antidotes, antiemetic/antivertigo agents, antifungals, antigonadotropic agents, antigout agents, antihistamines, antihyperlipidemic agents, antihyperlipidemic combinations, antihypertensive combinations, antihyperuricemic agents, antimalarial agents, antimalarial combinations, antimalarial quinolones, antimanic agents, antimetabolites, antimigraine agents, antineoplastic combinations, antineoplastic detoxifying agents, antineoplastic interferons, antineoplastics, antiparkinson agents, antiplatelet agents, antipseudomonal penicillins, antipsoriatics, antipsychotics, antirheumatics, antiseptic and germicides, antithyroid agents, antitoxins and antivenins, antituberculosis agents, antituberculosis combinations, antitussives, antiviral agents, antiviral boosters, antiviral combinations, antiviral interferons, anxiolytics, sedatives, and hypnotics, aromatase inhibitors, atypical antipsychotics, azole antifungals, bacterial vaccines, barbiturate anticonvulsants, barbiturates, BCR-ABL tyrosine kinase inhibitors, benzodiazepine anticonvulsants, benzodiazepines, beta blockers with calcium channel blockers, beta blockers with thiazides, beta-adrenergic blocking agents, beta-lactamase inhibitors, bile acid sequestrants, biologicals, bisphosphonates, bone morphogenetic proteins, bone resorption inhibitors, bronchodilator combinations, bronchodilators, calcimimetics, calcineurin inhibitors, calcitonin, calcium channel blocking agents, carbamate anticonvulsants, carbapenems, carbapenems/beta-lactamase inhibitors, carbonic anhydrase inhibitor anticonvulsants, carbonic anhydrase inhibitors, cardiac stressing agents, cardioselective beta blockers, cardiovascular agents, catecholamines, cation exchange resins, CD20 monoclonal antibodies, CD30 monoclonal antibodies, CD33 monoclonal antibodies, CD38 monoclonal antibodies, CD52 monoclonal antibodies, CDK 4/6 inhibitors, central nervous system agents, cephalosporins, cephalosporins/beta-lactamase inhibitors, cerumenolytics, CFTR combinations, CFTR potentiators, CGRP inhibitors, chelating agents, chemokine receptor antagonist, chloride channel activators, cholesterol absorption inhibitors, cholinergic agonists, cholinergic muscle stimulants, cholinesterase inhibitors, CNS stimulants, coagulation modifiers, colony stimulating factors, contraceptives, corticotropin, coumarins and indandiones, cox-2 inhibitors, decongestants, dermatological agents, diagnostic radiopharmaceuticals, diarylquinolines, dibenzazepine anticonvulsants, digestive enzymes, dipeptidyl peptidase 4 inhibitors, diuretics, dopaminergic antiparkinsonism agents, drugs used in alcohol dependence, echinocandins, EGFR inhibitors, estrogen receptor antagonists, estrogens, expectorants, factor Xa inhibitors, fatty acid derivative anticonvulsants, fibric acid derivatives, first generation cephalosporins, fourth generation cephalosporins, functional bowel disorder agents, gallstone solubilizing agents, gamma-aminobutyric acid analogs, gamma-aminobutyric acid reuptake inhibitors, gastrointestinal agents, general anesthetics, genitourinary tract agents, GI stimulants, glucocorticoids, glucose elevating agents, glycopeptide antibiotics, glycoprotein platelet inhibitors, glycylcyclines, gonadotropin releasing hormones, gonadotropin-releasing hormone antagonists, gonadotropins, group I antiarrhythmics, group II antiarrhythmics, group III antiarrhythmics, group IV antiarrhythmics, group V antiarrhythmics, growth hormone receptor blockers, growth hormones, guanylate cyclase-C agonists, *H. pylori* eradication agents, H2 antagonists, hedgehog pathway inhibitors, hematopoietic stem cell mobilizer, heparin antagonists, heparins, HER2 inhibitors, herbal products, histone deacetylase inhibitors, hormones, hormones/antineoplastics, hydantoin anticonvulsants, hydrazide derivatives, illicit (street) drugs, immune globulins, immunologic agents, immunostimulants, immunosuppressive agents, impotence agents, in vivo diagnostic biologicals, incretin mimetics, inhaled anti-infectives, inhaled corticosteroids, inotropic agents, insulin, insulin-like growth factors, integrase strand transfer inhibitor, interferons, interleukin inhibitors, interleukins, intravenous nutritional products, iodinated contrast media, ionic iodinated contrast media, iron products, ketolides, laxatives, leprostatics, leukotriene modifiers, lincomycin derivatives, local injectable anesthetics, local injectable anesthetics with corticosteroids, loop diuretics, lung surfactants, lymphatic staining agents, lysosomal enzymes, macrolide derivatives, macrolides, magnetic resonance imaging contrast media, mast cell stabilizers, medical gas, meglitinides, metabolic agents, methylxanthines, mineralocorticoids, minerals and electrolytes, miscellaneous agents, miscellaneous analgesics, miscellaneous antibiotics, miscellaneous anticonvulsants, miscellaneous antidepressants, miscellaneous antidiabetic agents, miscellaneous antiemetics, miscellaneous antifungals, miscellaneous antihyperlipidemic agents, miscellaneous antihypertensive combinations, miscellaneous antimalarials, miscellaneous antineoplastics, miscellaneous antiparkinson agents, miscellaneous antipsychotic agents, miscellaneous antituberculosis agents, miscellaneous antivirals, miscellaneous anxiolytics, sedatives and hypnotics, miscellaneous bone resorption inhibitors, miscellaneous cardiovascular agents, miscellaneous central nervous system agents, miscellaneous coagulation modifiers, miscellaneous diagnostic dyes, miscellaneous diuretics, miscellaneous genitourinary tract agents, miscellaneous GI agents, miscellaneous hormones, miscellaneous metabolic agents, miscellaneous ophthalmic agents, miscellaneous otic agents, miscellaneous respiratory agents, miscellaneous sex hormones, miscellaneous topical agents, miscellaneous uncategorized agents, miscellaneous vaginal agents, mitotic inhibitors, monoamine oxidase inhibitors, mouth and throat products, mTOR inhibitors, mucolytics, multikinase inhibitors, muscle relaxants, mydriatics, narcotic analgesic combinations, narcotic analgesics, nasal anti-infectives, nasal antihistamines and decongestants, nasal lubricants and irrigations, nasal preparations, nasal steroids, natural penicillins, neprilysin inhibitors, neuraminidase inhibitors, neuromuscular blocking agents, neuronal potassium channel openers, next generation cephalosporins, nicotinic acid derivatives, NK1 receptor antagonists, NNRTIs, non-cardioselective beta blockers, non-iodinated contrast media, non-ionic iodinated contrast media, non-sulfonylureas, Nonsteroidal anti-inflammatory drugs, NS5A inhibitors, nucleoside reverse transcriptase inhibitors (NRTIs), nutraceutical products, nutritional products, ophthalmic anesthetics, ophthalmic anti-infectives, ophthalmic anti-inflammatory agents, ophthalmic antihistamines and decongestants, ophthalmic diagnostic agents, ophthalmic glaucoma agents, ophthalmic lubricants and irrigations, ophthalmic preparations, ophthalmic steroids, ophthalmic steroids with anti-infectives, ophthalmic surgical agents, oral nutritional supplements, other immunostimulants, other immunosuppressants, otic anesthetics, otic anti-infectives, otic preparations, otic steroids, otic steroids with anti-infectives, oxazolidinedione anticonvulsants, oxazolidinone antibiotics, parathyroid hormone and analogs, PARP inhibitors, PCSK9 inhibitors, penicillinase resistant penicillins, penicillins, peripheral opioid receptor antagonists, peripheral opioid receptor mixed agonists/antagonists, peripheral vasodilators, peripherally acting antiobesity agents, phenothiazine antiemetics, phenothiazine antipsychotics, phenylpiperazine antidepressants, phosphate binders, PI3K inhibitors, plasma expanders, platelet aggregation inhibitors, platelet-stimulating agents, polyenes, potassium sparing diuretics with thiazides, potassium-sparing diuretics, probiotics, progesterone receptor modulators, progestins, prolactin inhibitors, prostaglandin D2 antagonists, protease inhibitors, protease-activated receptor-1 antagonists, proteasome inhibitors, proton pump inhibitors, psoralens, psychotherapeutic agents, psychotherapeutic combinations, purine nucleosides, pyrrolidine anticonvulsants, quinolones, radiocontrast agents, radiologic adjuncts, radiologic agents, radiologic conjugating agents, radiopharmaceuticals, recombinant human erythropoietins, renin inhibitors, respiratory agents, respiratory inhalant products, rifamycin derivatives, salicylates, sclerosing agents, second generation cephalosporins, selective estrogen receptor modulators, selective immunosuppressants, selective phosphodiesterase-4 inhibitors, selective serotonin reuptake inhibitors, serotonin-norepinephrine reuptake inhibitors, serotoninergic neuroenteric modulators, sex hormone combinations, sex hormones, SGLT-2 inhibitors, skeletal muscle relaxant combinations, skeletal muscle relaxants, smoking cessation agents, somatostatin and somatostatin analogs, spermicides, statins, sterile irrigating solutions, streptogramins, streptomyces derivatives, succinimide anticonvulsants, sulfonamides, sulfonylureas, synthetic ovulation stimulants, tetracyclic antidepressants, tetracyclines, therapeutic radiopharmaceuticals, therapeutic vaccines, thiazide diuretics, thiazolidinediones, thioxanthenes, third generation cephalosporins, thrombin inhibitors, thrombolytics, thyroid drugs, TNF alfa inhibitors, tocolytic agents, topical acne agents, topical agents, topical allergy diagnostic agents, topical anesthetics, topical anti-infectives, topical anti-rosacea agents, topical antibiotics, topical antifungals, topical antihistamines, topical antineoplastics, topical antipsoriatics, topical antivirals, topical astringents, topical debriding agents, topical depigmenting agents, topical emollients, topical keratolytics, topical non-steroidal anti-inflammatories, topical photochemotherapeutics, topical rubefacient, topical steroids, topical steroids with anti-infectives, transthyretin stabilizers, triazine anticonvulsants, tricyclic antidepressants, trifunctional monoclonal antibodies, ultrasound contrast media, upper respiratory combinations, urea anticonvulsants, urea cycle disorder agents, urinary anti-infectives, urinary antispasmodics, urinary pH modifiers, uterotonic agents, vaccine combinations, vaginal anti-infectives, vaginal preparations, vasodilators, vasopressin antagonists, vasopressors, VEGF/VEGFR inhibitors, viral vaccines, viscosupplementation agents, vitamin and mineral combinations, vitamins, or VMAT2 inhibitors. The drug administration devices of the present disclosure may administer a drug selected from epinephrine, Rebif, Enbrel, Aranesp, atropine, pralidoxime chloride, diazepam, insulin, antropine sulfate, avibactam sodium, bendamustine hydrochloride, carboplatin, daptomycin, epinephrine, levetiracetam, oxaliplatin, paclitaxel, pantoprazole sodium, treprostinil, vasopressin, voriconazole, zoledronic acid, mometasone, fluticasone, ciclesonide, budesonide, beclomethasone, vilanterol, salmeterol, formoterol, umeclidinium, glycopyrrolate, tiotropium, aclidinium, indacaterol, salmeterol, and olodaterol.

As mentioned above, any of a variety of drugs can be delivered using a drug administration device.

Drug Housings

As described above, a dosage form can be provided in a holder that is appropriate for the particular dosage form being utilized. For example, a drug in a liquid dosage form can be held prior to administration within a holder in the form of a vial with a stopper, or a syringe with a plunger. A drug in solid or powder dosage form, e.g., as tablets, can be contained in a housing which is arranged to hold the tablets securely prior to administration.

The housing can include one or a plurality of drug holders, where each holder contains a dosage form, e.g., the drug can be in a tablet dosage form and the housing can be in the form of a blister pack, where a tablet is held within each of a plurality of holders. The holders being in the form of recesses in the blister pack.

Figure 6:
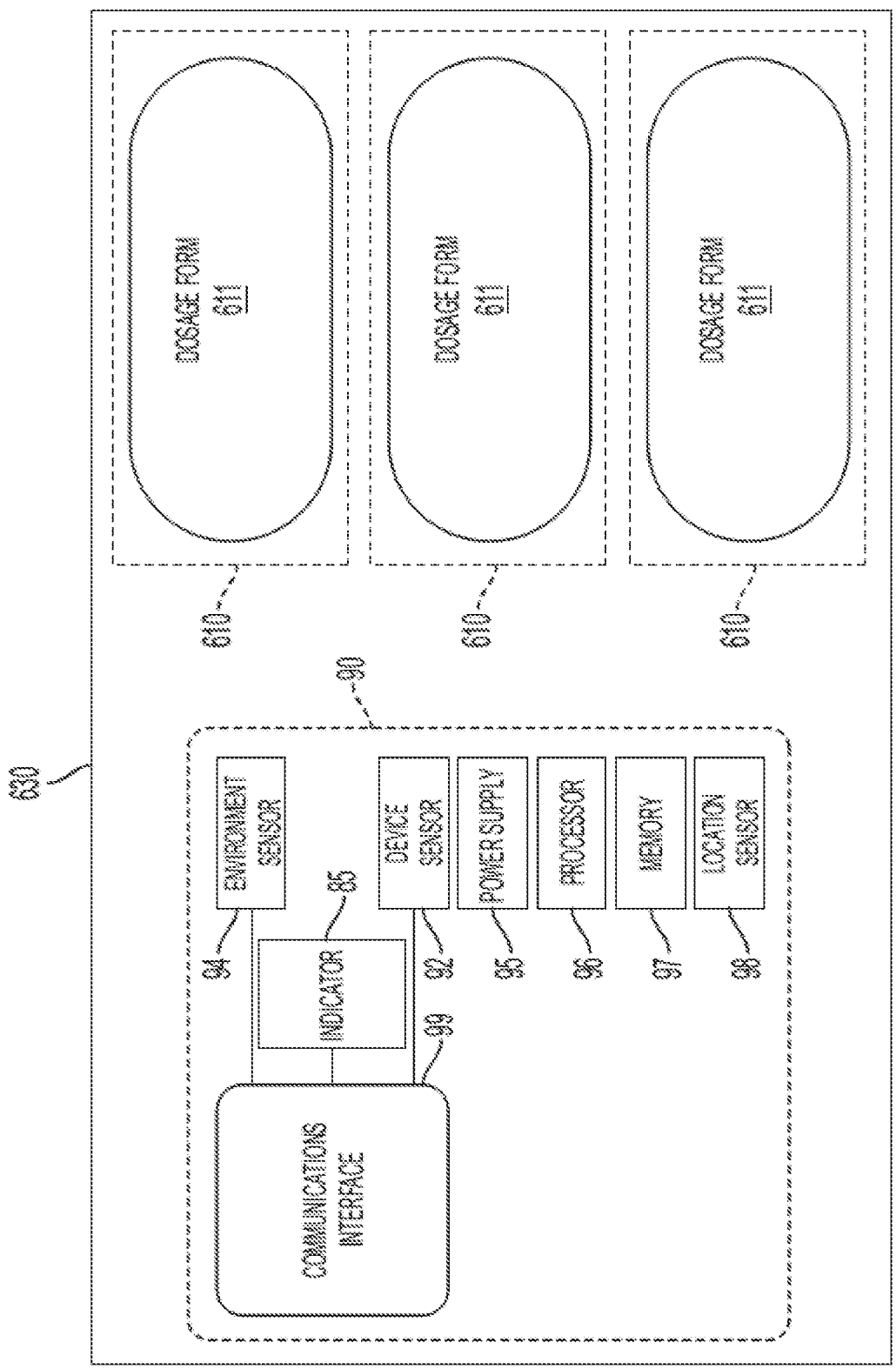
FIG. 6 is a schematic view of one embodiment of a housing for a dosage form.

FIG. 6 depicts a housing 630 that includes a plurality of drug holders 610 that each contain a dosage form 611. The housing 630 can have at least one environment sensor 94, which is configured to sense information relating to the environment in which the housing 630 is present, such as the temperature of the environment, time or location. The housing 630 can include at least one device sensor 92, which is configured to sense information relating to the drug of the dosage form 611 contained within the holder 610. There can be a dedicated location sensor 98 which is configured to determine the geographical location of the housing 630, e.g., via satellite position determination, such as GPS.

The housing 630 can include an indicator 85 which is configured to present information about the status of the drug of the dosage form 611 contained within the holder 610 to a user of the drug housing. The housing 630 can also include a communications interface 99 which can communicate information externally via a wired or wireless transfer of data pertaining to the drug housing 630, environment, time, or location and/or the drug itself.

If required, the housing 630 can include a power supply 95 for delivering electrical power to one or more electrical components of the housing 630. The power supply 95 can be a source of power which is integral to housing 630 and/or a mechanism for connecting the housing 630 to an external source of power. The housing 630 can also include a computer system 90 including a processor 96 and a memory 97 powered by the power supply 95 and in communication with each other, and optionally with other electrical and control components of the housing 630, such as the environment sensor 94, the location sensor 98, the device sensor 92, the communications interface 99, and/or the indicator 85. The processor 96 is configured to obtain data acquired from the environment sensor 94, the device sensor 92, the communications interface 99, the location sensor 98, and/or the user interface 80 and process it to provide data output, for example to the indicator 85 and/or to the communications interface 99.

The housing 630 can be in the form of packaging. Alternatively, additional packaging can be present to contain and surround the housing 630.

The holder 610 or the additional packaging the themselves include one or more of the device sensor 92, the environment sensor 94, the indicator 85, the communications interface 99, the power supply 95, location sensor 98, and the computer system including the processor 96 and the memory 85, as described above.

Electronic Communication

Figure 7:
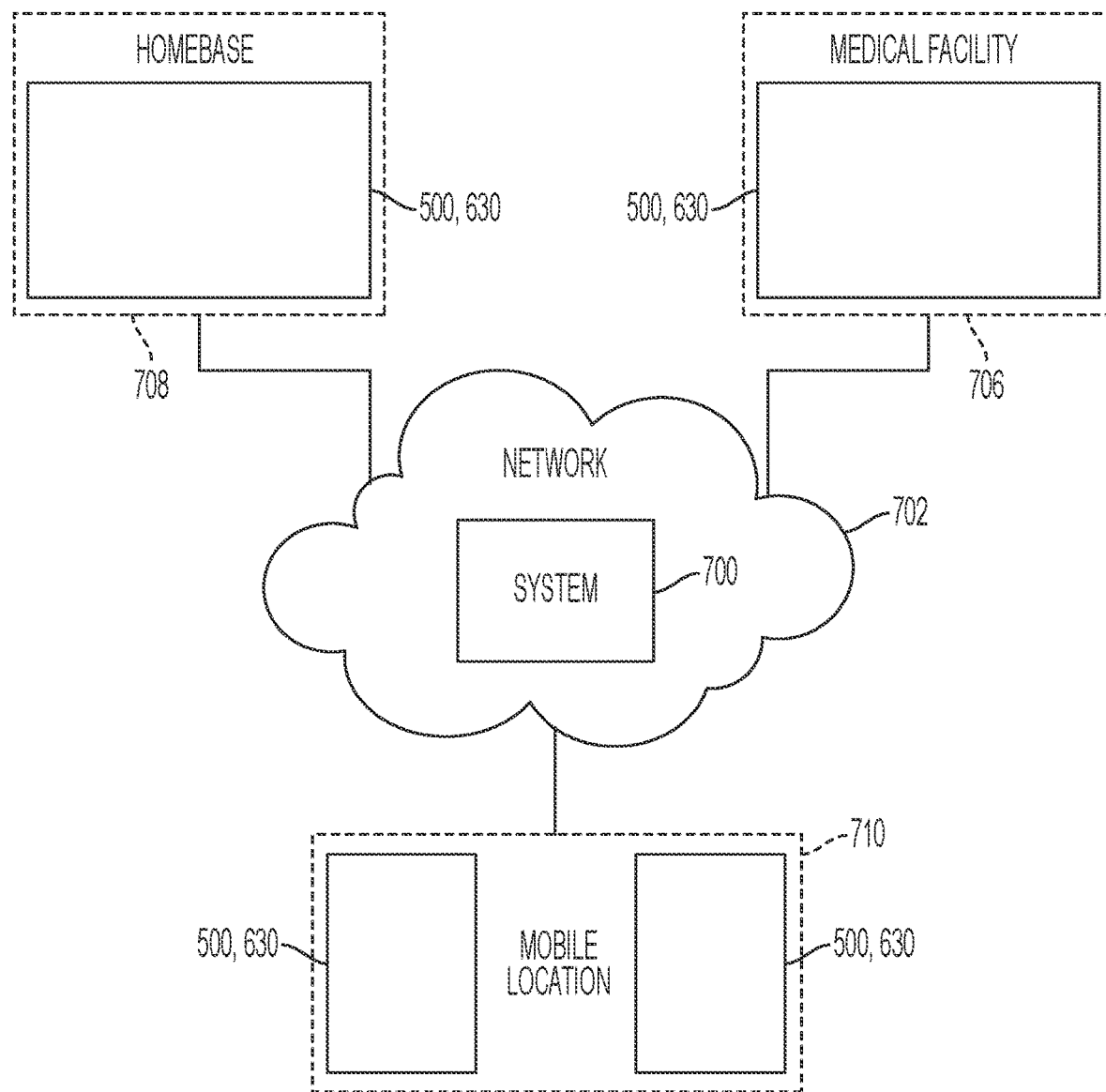
FIG. 7 is a schematic view of one embodiment of a communication network system with which the drug administration devices and housing can operate.

As mentioned above, the communications interface 99 can be associated with the drug administration device 500 or the drug housing 630, by being included within or on the housing 30, 630, or alternatively within or on the packaging 35. Such a communications interface 99 can be configured to communicate with a remote computer system, such as central computer system 700 shown in FIG. 7. As shown in FIG. 7, the communications interface 99 associated with the drug administration device 500 or the housing 630 is configured to communicate with a central computer system 700 through a communications network 702 from any number of locations such as a medical facility 706 (e.g., a hospital or other medical care center), a home base 708 (e.g., a patient's home or office or a care taker's home or office), or a mobile location 710. The communications interface 99 can be configured to access the system 700 through a wired and/or wireless connection to the network 702. In an exemplary embodiment, the communications interface 99 of FIG. 6 is configured to access the system 700 wirelessly, e.g., through Wi-Fi connection(s), which can facilitate accessibility of the system 700 from almost any location in the world.

A person skilled in the art will appreciate that the system 700 can include security features such that the aspects of the system 700 available to any particular user can be determined based on, e.g., the identity of the user and/or the location from which the user is accessing the system. To that end, each user can have a unique username, password, biometric data, and/or other security credentials to facilitate access to the system 700. The received security parameter information can be checked against a database of authorized users to determine whether the user is authorized and to what extent the user is permitted to interact with the system, view information stored in the system, and so forth.

Computer Systems

As discussed herein, one or more aspects or features of the subject matter described herein, for example components of the central computer system 700, the processor 96, the power supply 95, the memory 97, the communications interface 99, the user interface 80, the device indicators 85, the device sensors 92, the environment sensors 94, and the location sensors 98, can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system can include clients and servers. A client and server are generally remote from each other and typically interact through a communications network, e.g., the Internet, a wireless wide area network, a local area network, a wide area network, or a wired network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" as used herein refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein, for example the user interface 80 (which can be integrated or separate to the administration device 500 or the housing 630), can be implemented on a computer having a display screen, such as for example a cathode ray tube (CRT) or a liquid crystal display (LCD) or a light emitting diode (LED) monitor for displaying information to the user. The display screen can allow input thereto directly (e.g., as a touch screen) or indirectly (e.g., via an input device such as a keypad or voice recognition hardware and software). Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. As described above, this feedback may be provided via one or more device indicators 85 in addition to the user interface 80. The device indicators 85 can interact with one or more of the device sensor(s) 92, the environment sensor(s) 94, and/or the location sensor(s) 98 in order to provide this feedback, or to receive input from the user.

Figure 8:
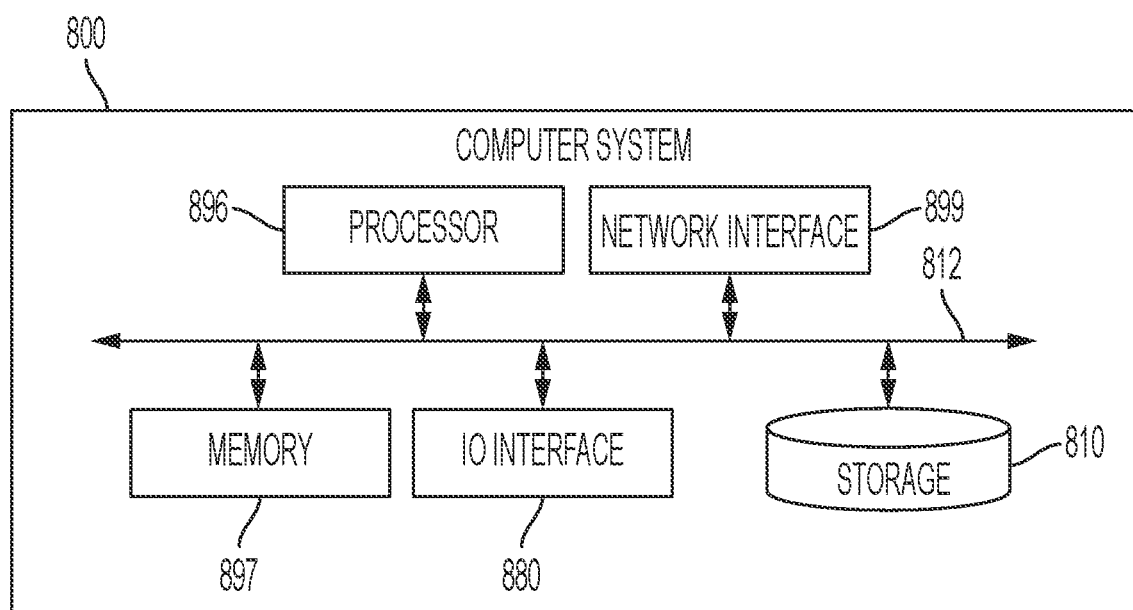
FIG. 8 is a schematic view of one embodiment of a computer system with which the drug administration devices and housing can operate.

FIG. 8 illustrates one exemplary embodiment of the computer system 700, depicted as computer system 800. The computer system includes one or more processors 896 configured to control the operation of the computer system 800. The processor(s) 896 can include any type of microprocessor or central processing unit (CPU), including programmable general-purpose or special-purpose microprocessors and/or any one of a variety of proprietary or commercially available single or multi-processor systems.

The computer system 800 also includes one or more memories 897 configured to provide temporary storage for code to be executed by the processor(s) 896 or for data acquired from one or more users, storage devices, and/or databases. The memory 897 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system are coupled to a bus system 812. The illustrated bus system 812 is an abstraction that represents any one or more separate physical busses, communication lines/interfaces, and/or multi-drop or point-to-point connections, connected by appropriate bridges, adapters, and/or controllers. The computer system 800 also includes one or more network interface(s) 899 (also referred to herein as a communications interface), one or more input/output (IO) interface(s) 880, and one or more storage device(s) 810.

The communications interface(s) 899 are configured to enable the computer system to communicate with remote devices, e.g., other computer systems and/or devices 500 or housings 630, over a network, and can be, for example, remote desktop connection interfaces, Ethernet adapters, and/or other local area network (LAN) adapters. The IO interface(s) 880 include one or more interface components to connect the computer system 800 with other electronic equipment. For example, the IO interface(s) 880 can include high speed data ports, such as universal serial bus (USB) ports, 1394 ports, Wi-Fi, Bluetooth, etc. Additionally, the computer system 800 can be accessible to a human user, and thus the IO interface(s) 880 can include displays, speakers, keyboards, pointing devices, and/or various other video, audio, or alphanumeric interfaces. The storage device(s) 810 include any conventional medium for storing data in a non-volatile and/or non-transient manner. The storage device(s) 810 are thus configured to hold data and/or instructions in a persistent state in which the value(s) are retained despite interruption of power to the computer system. The storage device(s) 810 can include one or more hard disk drives, flash drives, USB drives, optical drives, various media cards, diskettes, compact discs, and/or any combination thereof and can be directly connected to the computer system or remotely connected thereto, such as over a network. In an exemplary embodiment, the storage device(s) 810 include a tangible or non-transitory computer readable medium configured to store data, e.g., a hard disk drive, a flash drive, a USB drive, an optical drive, a media card, a diskette, or a compact disc.

The elements illustrated in FIG. 8 can be some or all of the elements of a single physical machine. In addition, not all of the illustrated elements need to be located on or in the same physical machine.

The computer system 800 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 800 can also include a web server for generating and/or delivering the web pages to client computer systems.

As shown in FIG. 7, the computer system 800 of FIG. 8 as described above may form the components of the central computer system 700 which is in communication with one or more of the device computer systems 90 of the one or more individual drug administration devices 500 or housings 630 and/or in communication with one or more other elements, such as one or more surgical instruments. Data, such as operational data of the devices 500 or housings 630, medical data acquired of patients by such devices 500 or housings 630, operational data of the surgical instruments, medical data acquired of patients by such surgical instruments, can be exchanged between the central and device computer systems 700, 90.

As mentioned the computer system 800 as described above can also form the components of a device computer system 90 which is integrated into or in close proximity to the drug administration device 500 or housing 630. In this regard, the one or more processors 896 correspond to the processor 96, the network interface 799 corresponds to the communications interface 99, the IO interface 880 corresponds to the user interface 80, and the memory 897 corresponds to the memory 97. Moreover, the additional storage 810 can also be present in device computer system 90.

In an exemplary embodiment, the computer system 800 can form the device computer system 90 as a single unit, e.g., contained within a single drug administration device housing 30, contained within a single package 35 for one or more drug administration devices 500, or a housing 630 that includes a plurality of drug holders 610. The computer system 800 can form the central computer system 700 as a single unit, as a single server, or as a single tower.

The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system can also include any of a variety of other software and/or hardware components, including by way of example, operating systems and database management systems. Although an exemplary computer system is depicted and described herein, it will be appreciated by a person skilled in the art that this is for sake of generality and convenience. In other embodiments, the computer system may differ in architecture and operation from that shown and described here. For example, the memory 897 and the storage device 810 can be integrated together, or the communications interface 899 can be omitted if communication with another computer system is not necessary.

Surgical Hubs

In an exemplary embodiment, the computer system to which data regarding drug administration devices and/or surgical instruments is communicated includes a surgical hub. Exemplary examples of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0207857 entitled "Surgical Network Determination Of Prioritization Of Communication, Interaction, Or Processing Based On System Or Device Needs" filed Nov. 6, 2018, and U.S. Pat. Pub. No. 2019/0206555 entitled "Cloud-based Medical Analytics For Customization And Recommendations To A User" filed Mar. 29, 2018, which are hereby incorporated by reference in their entireties.

In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as one or more surgical instruments that are used to conduct medical procedures on patients and/or one or more drug administration device that are used to administer one or more drugs to patients during performance of medical procedures. The surgical hubs provide a wide array of functionality to improve the outcomes of medical procedures. The data generated by the various surgical devices, drug administration devices, and surgical hubs about the patient and the medical procedure may be transmitted to the cloud-based medical analytics system. This data may then be aggregated with similar data gathered from many other surgical hubs, drug administration devices, and surgical instruments located at other medical facilities. Various patterns and correlations may be found through the cloud-based analytics system analyzing the collected data. Improvements in the techniques used to generate the data may be generated as a result, and these improvements may then be disseminated to the various surgical hubs, drug administration devices, and surgical instruments. Due to the interconnectedness of all of the aforementioned components, improvements in medical procedures and practices may be found that otherwise may not be found if the many components were not so interconnected. Various examples of structures and functions of these various components are described in more detail in previously mentioned U.S. Pat. Pub. No. 2019/0200844 entitled "Method Of Hub Communication, Processing, Storage And Display" filed Dec. 4, 2018, U.S. Pat. Pub. No. 2019/0207857 entitled "Surgical Network Determination Of Prioritization Of Communication, Interaction, Or Processing Based On System Or Device Needs" filed Nov. 6, 2018, and U.S. Pat. Pub. No. 2019/006555 entitled "Cloud-based Medical Analytics For Customization And Recommendations To A User" filed Mar. 29, 2018.

Figure 9:
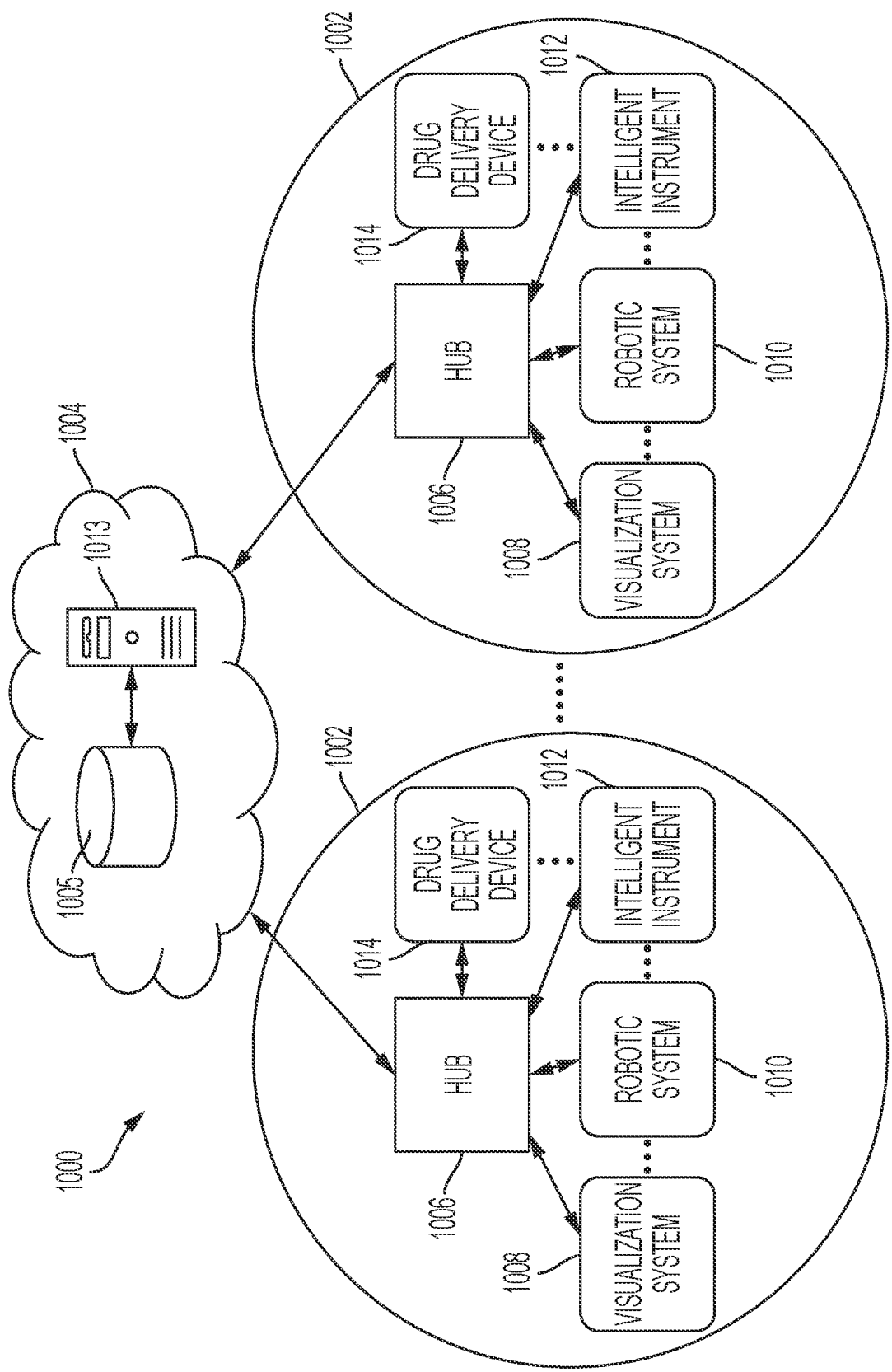
FIG. 9 is a schematic view of one embodiment of a computer-implemented interactive surgical system.

FIG. 9 illustrates an embodiment of a computer-implemented interactive surgical system 1000 that includes one or more surgical systems 1002 and a cloud-based system (e.g., a cloud 1004 that can include a remote server 1013 coupled to a storage device 1005). Each surgical system 1002 includes at least one surgical hub 1006 in communication with the cloud 1004. In one example, as illustrated in FIG. 9, the surgical system 1002 includes a visualization system 1008, a robotic system 1010, a handheld intelligent surgical instrument 1012, and a drug delivery device 1014, which are configured to communicate with one another and/or the hub 1006. The surgical system 1002 can include an M number of hubs 1006, an N number of visualization systems 1008, an O number of robotic systems 1010, a P number of handheld intelligent surgical instruments 1012, and a Q number of drug delivery devices 1014, where M, N, O, P, and Q are integers greater than or equal to one that may or may not be equal to any one or more of each other. Various exemplary drug delivery devices are described above. Various exemplary examples of suitable robotic systems, visualization systems, cloud-based analytics, and surgical instruments that can be used in a computer-implemented interactive surgical system are further described in previously mentioned U.S. Pat. Pub. No. 2019/0200844 entitled "Method Of Hub Communication, Processing, Storage And Display" filed Dec. 4, 2018, U.S. Pat. Pub. No. 2019/0207857 entitled "Surgical Network Determination Of Prioritization Of Communication, Interaction, Or Processing Based On System Or Device Needs" filed Nov. 6, 2018, and U.S. Pat. Pub. No. 2019/006555 entitled "Cloud-based Medical Analytics For Customization And Recommendations To A User" filed Mar. 29, 2018.

Figure 10:
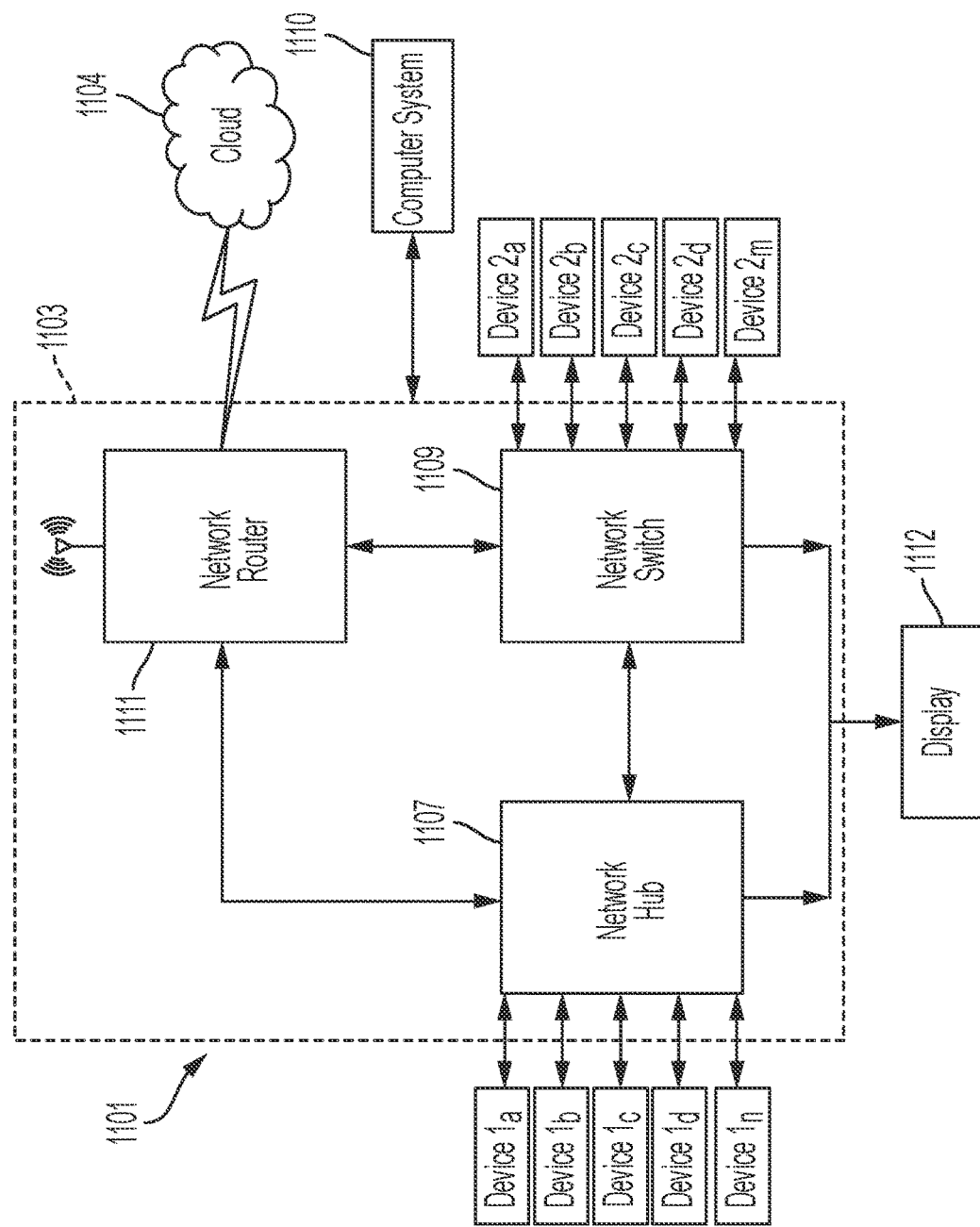
FIG. 10 is a schematic view of one embodiment of a surgical data network.

FIG. 10 illustrates one example of a surgical data network 1101 including a modular communication hub 1103, e.g., the hub 1006, configured to connect modular devices located in one or more operating theaters of a healthcare facility, or any room in a healthcare facility specially equipped for surgical operations, to a cloud-based system including the cloud 1104 that includes a remote server coupled to a storage device, e.g., the cloud 1004 that includes the remote server coupled to the storage device 1005. The modular communication hub 1103 includes a network hub 1107 and/or a network switch 1109 in communication with a network router 1111. The network hub 1107, the network switch 1109, and the network router 1111 define the communication hub's communications interface. The modular communication hub 1103 also can be coupled to a local computer system 1110 to provide local computer processing and data manipulation. The surgical data network 1101 can be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 1107 or network switch 1109. An "intelligent surgical data network" may be referred to as a "manageable hub" or "manageable switch." A switching hub reads the destination address of each packet and then forwards the packet to the correct port.

Modular devices $1_a$-$1_n$, e.g., any number of surgical instruments such as instruments 1012 and/or any number of drug delivery devices such as devices 1014, located in the operating theater can be coupled to the modular communication hub 1103. The network hub 1107 and/or the network switch 1109 can be coupled to a network router 1111 to connect the devices $1_a$-$1_n$ to the cloud 1104 or the local computer system 1110. Data associated with the devices $1_a$-$1_n$ can be transferred to cloud-based computers via the router for remote data processing and manipulation. Data associated with the devices $1_a$-$1_n$ can also be transferred to the local computer system 1110 for local data processing and manipulation. Modular devices $2_a$-$2_m$ located in the same operating theater also can be coupled to a network switch 1109. The network switch 1109 can be coupled to the network hub 1107 and/or the network router 1111 to connect to the devices $2_a$-$2_m$ to the cloud 1104. Data associated with the devices $2_a$-$2_m$ can be transferred to the cloud 1104 via the network router 1111 for data processing and manipulation. Data associated with the devices $2_a$-$2_m$ can also be transferred to the local computer system 1110 for local data processing and manipulation. The numbers n, m of the devices $1_a$-$1_n$/$2_a$-$2_m$ can be the same as or different from one another.

A person skilled in the art will appreciate that the surgical data network 1101 can be expanded by interconnecting multiple network hubs 1107 and/or multiple network switches 1109 with multiple network routers 1111. The modular communication hub 1103 can be contained in a modular control tower configured to receive multiple devices $1_a$-$1_n$/$2_a$-$2_m$. The local computer system 1110 also can be contained in a modular control tower. The modular communication hub 1103 is connected to a display 1112 to display images obtained by at least some of the devices $1_a$-$1_n$/$2_a$-$2_m$, for example during surgical procedures.

The surgical data network 1101 can include a combination of network hub(s), network switch(es), and network router(s) connecting the devices $1_a$-$1_n$/$2_a$-$2_m$ the cloud 1104. Any one of or all of the devices $1_a$-$1_n$/$2_a$-$2_m$ coupled to the network hub 1107 or network switch 1109 can collect data in real time and transfer the data to cloud computers for data processing and manipulation. Alternatively or in addition, any one or all of the devices $1_a$-$1_n$/$2_a$-$2_m$ coupled to the network hub 1107 or network switch 1109 can transfer previously collected data, such as sensor data, to cloud computers for data processing and manipulation, e.g., once the one or all of the devices $1_a$-$1_n$/$2_a$-$2_m$ is operatively connected to the cloud 1104 via the communication hub 1103. A person skilled in the art will appreciate that cloud computing relies on sharing computing resources rather than having local servers or personal devices to handle software applications. The term "cloud" can be used as a metaphor for "the Internet," although the term is not limited as such. Accordingly, the term "cloud computing" may be used herein to refer to "a type of Internet-based computing," where different services, such as servers, storage, and applications, are delivered to the modular communication hub 1103 and/or the computer system 1110 located in the surgical theater (e.g., a fixed, mobile, temporary, or field operating room or space) and to devices connected to the modular communication hub 1103 and/or the computer system 1110 through the Internet. The cloud infrastructure can be maintained by a cloud service provider. In this context, the cloud service provider can be the entity that coordinates the usage and control of the devices $1_a$-$1_n$/$2_a$-$2_m$ located in one or more operating theaters. The cloud computing services can perform a large number of calculations based on the data gathered by smart surgical instruments, smart drug delivery devices, robots, and other computerized devices located in the operating theater. The hub hardware enables multiple devices or connections to be connected to a computer that communicates with the cloud computing resources and storage.

Applying cloud computer data processing techniques on the data collected by the devices $1_a$-$1_n$/$2_a$-$2_m$ the surgical data network may provide improved surgical outcomes, reduced costs, and/or improved patient satisfaction. At least some of the devices $1_a$-$1_n$/$2_a$-$2_m$, e.g., one or more of the surgical instruments 1012, can be employed to view tissue states to assess leaks or perfusion of sealed tissue after a tissue sealing and cutting procedure. At least some of the devices $1_a$-$1_n$/$2_a$-$2_m$, e.g., one or more of the surgical instruments 1012, can be employed to identify pathology, such as the effects of diseases, using the cloud-based computing to examine data including images of samples of body tissue for diagnostic purposes. This includes localization and margin confirmation of tissue and phenotypes. At least some of the devices $1_a$-$1_n$/$2_a$-$2_m$, e.g., one or more of the surgical instruments 1012, can be employed to identify anatomical structures of the body using a variety of sensors integrated with imaging devices and techniques such as overlaying images captured by multiple imaging devices. At least some of the devices $1_a$-$1_n$/$2_a$-$2_m$, e.g., one or more of the drug delivery devices 1014, can be employed to identify dimensions of a patient's bariatric sleeve in bariatric surgical intervention using, e.g., an insulin pump, to facilitate visualization of the sleeve. The data gathered by the devices $1_a$-$1_n$/$2_a$-$2_m$, including image data, can be transferred to the cloud 1104 or the local computer system 1110 or both for data processing and manipulation including image processing and manipulation. The data can be analyzed to improve surgical procedure outcomes by determining if further treatment, such as the application of endoscopic intervention, emerging technologies, a targeted radiation, targeted intervention, precise robotics to tissue-specific sites and conditions, and drug administration may be pursued. Such data analysis can further employ outcome analytics processing, and using standardized approaches may provide beneficial feedback to either confirm surgical treatments and the behavior of the surgeon or suggest modifications to surgical treatments, surgeon behavior, drug delivery devices, and/or drugs.

The operating theater devices $1_a$-$1_n$ can be connected to the modular communication hub 1103 over a wired channel or a wireless channel depending on the configuration of the devices $1_a$-$1_n$ to a network hub. The network hub 1107 can be implemented as a local network broadcast device that works on the physical layer of the Open System Interconnection (OSI) model. The network hub provides connectivity to the devices $1_a$-$1_n$ located in the same operating theater network. The network hub 1107 collects data in the form of packets and sends them to the router 1111 in half duplex mode. The network hub 1107 does not store any media access control/Internet Protocol (MAC/IP) to transfer the device data. Only one of the devices $1_a$-$1_n$ can send data at a time through the network hub 1107. The network hub 1107 has no routing tables or intelligence regarding where to send information and broadcasts all network data across each connection and to a remote server over the cloud 1104. The network hub 1107 can detect basic network errors such as collisions, but having all information broadcast to multiple ports can be a security risk and cause bottlenecks.

The operating theater devices $2_a$-$2_m$ can be connected to a network switch 1109 over a wired channel or a wireless channel. The network switch 1109 works in the data link layer of the OSI model. The network switch 1109 is a multicast device for connecting the devices $2_a$-$2_m$ located in the same operating theater to the network. The network switch 1109 sends data in the form of frames to the network router 1111 and works in full duplex mode. Multiple devices $2_a$-$2_m$ can send data at the same time through the network switch 1109. The network switch 1109 stores and uses MAC addresses of the devices $2_a$-$2_m$ to transfer data.

The network hub 1107 and/or the network switch 1109 are coupled to the network router 1111 for connection to the cloud 1104. The network router 1111 works in the network layer of the OSI model. The network router 1111 creates a route for transmitting data packets received from the network hub 1107 and/or the network switch 1111 to cloud-based computer resources for further processing and manipulation of the data collected by any one of or all the devices $1_a$-$1_n$/$2_a$-$2_m$. The network router 1111 can be employed to connect two or more different networks located in different locations, such as, for example, different operating theaters of the same healthcare facility or different networks located in different operating theaters of different healthcare facilities. The network router 1111 sends data in the form of packets to the cloud 1104 and works in full duplex mode. Multiple devices can send data at the same time. The network router 1111 uses IP addresses to transfer data.

In one example, the network hub 1107 can be implemented as a USB hub, which allows multiple USB devices to be connected to a host computer. The USB hub can expand a single USB port into several tiers so that there are more ports available to connect devices to the host system computer. The network hub 1107 can include wired or wireless capabilities to receive information over a wired channel or a wireless channel. A wireless USB short-range, high-bandwidth wireless radio communication protocol cab be employed for communication between the devices $1_a$-$1_n$ and devices $2_a$-$2_m$ located in the operating theater.

In other examples, the operating theater devices $1_a$-$1_n$/$2_a$-$2_m$ can communicate to the modular communication hub 1103 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices $1_a$-$1_n$/$2_a$-$2_m$ can communicate to the modular communication hub 1103 via a number of wireless or wired communication standards or protocols, including but not limited to Wi-Fi (IEEE 802.11 family), WiMAX (IEEE 802.16 family), IEEE 802.20, long-term evolution (LIE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module can include a plurality of communication modules. For example, a first communication module may be dedicated to shorter-range wireless communications such as Wi-Fi and Bluetooth, and a second communication module can be dedicated to longer-range wireless communications such as GPS, EDGE, GPRS, CDMA, WiMAX, LTE, Ev-DO, and others.

The modular communication hub 1103 can serve as a central connection for one or all of the operating theater devices $1_a$-$1_n$/$2_a$-$2_m$ and handle a data type known as frames. Frames carry the data generated by the devices $1_a$-$1_n$/$2_a$-$2_m$. When a frame is received by the modular communication hub 1103, it is amplified and transmitted to the network router 1111, which transfers the data to the cloud computing resources by using a number of wireless or wired communication standards or protocols, as described herein.

The modular communication hub 1103 can be used as a standalone device or be connected to compatible network hubs and network switches to form a larger network. The modular communication hub 1103 is generally easy to install, configure, and maintain, making it a good option for networking the operating theater devices $1_a$-$1_n$/$2_a$-$2_m$.

Drug Administration Device Data Handling And Analysis

Data received by surgical hubs from drug administration devices can be used in any of a variety of ways. In an exemplary embodiment, a surgical hub can receive data from a drug administration device in use with a patient in a surgical setting, e.g., in use in an operating room during performance of a surgical procedure.

The surgical hub can use the received data in any of one or more ways. The surgical hub can be configured to cause visualization of the received data to be provided in the surgical setting on a display so that medical professionals in the surgical setting can view the data and thereby receive an understanding of the operation of the drug administration device(s) in use in the surgical setting. Such information provided via visualization can include text and/or images indicating when any of the drug administration device(s) administered a drug to the patient, identifying which drug(s) have been administered to the patient by any of the drug administration device(s), indicating whether any of the drug administration device(s) encountered an error in attempting to deliver a drug to the patient, and other types of information.

The surgical hub can be configured to analyze the received data in real time with use of the drug administration devices and adjust control one or more of the drug administration devices and/or one or more surgical instruments in use with the patient based on the analysis of the received data. Such adjustment can include, for example, causing more of a drug previously delivered to the patient in the surgical setting to be delivered to the patient by one or more of the drug delivery devices, causing a drug not previously delivered to the patient in the surgical setting to be delivered to the patient by one or more of the drug delivery devices, adjusting one or operational control parameters of at the one or more surgical instruments, causing one or more sensors of one or more of the drug administration devices and/or of one or more surgical instruments to take a measurement to help gain an understanding of the patient's current physiological condition, current operational status of a drug administration device, and/or current operational status of a surgical instrument, and other adjustments. Examples of the operational control parameters include motor speed, cutting element speed, time, duration, and level of energy application. Controlling and adjusting operation of surgical instruments is described further in previously mentioned U.S. Pat. Pub. No. 2019/0200844 entitled "Method Of Hub Communication, Processing, Storage And Display" filed Dec. 4, 2018, U.S. Pat. Pub. No. 2019/0207857 entitled "Surgical Network Determination Of Prioritization Of Communication, Interaction, Or Processing Based On System Or Device Needs" filed Nov. 6, 2018, and U.S. Pat. Pub. No. 2019/006555 entitled "Cloud-based Medical Analytics For Customization And Recommendations To A User" filed Mar. 29, 2018. Controlling and adjusting operation of drug administration devices can be similarly accomplished.

The surgical hub can be configured to communicate the received data to a cloud for storage in the patient's electronic medical record (EMR). The EMR may thus include accurate information regarding drug(s) administered to the patient in the surgical setting. The cloud can be configured to analyze the data received from the hub with respect to the patient's EMR and transmit an alert to the surgical hub if any critical conditions are identified, such as an allergy of the patient to the drug delivered or to be delivered as indicated in the patient's EMR, harmful drug combinations involving the drug delivered or to be delivered given drug(s) currently being taken (e.g., prescribed) to the patient as indicated in the patient's EMR, a potential poor patient response to the drug delivered or to be delivered given one or more pre-existing conditions of the patient as indicated in the patient's EMR, etc.

Figure 11:
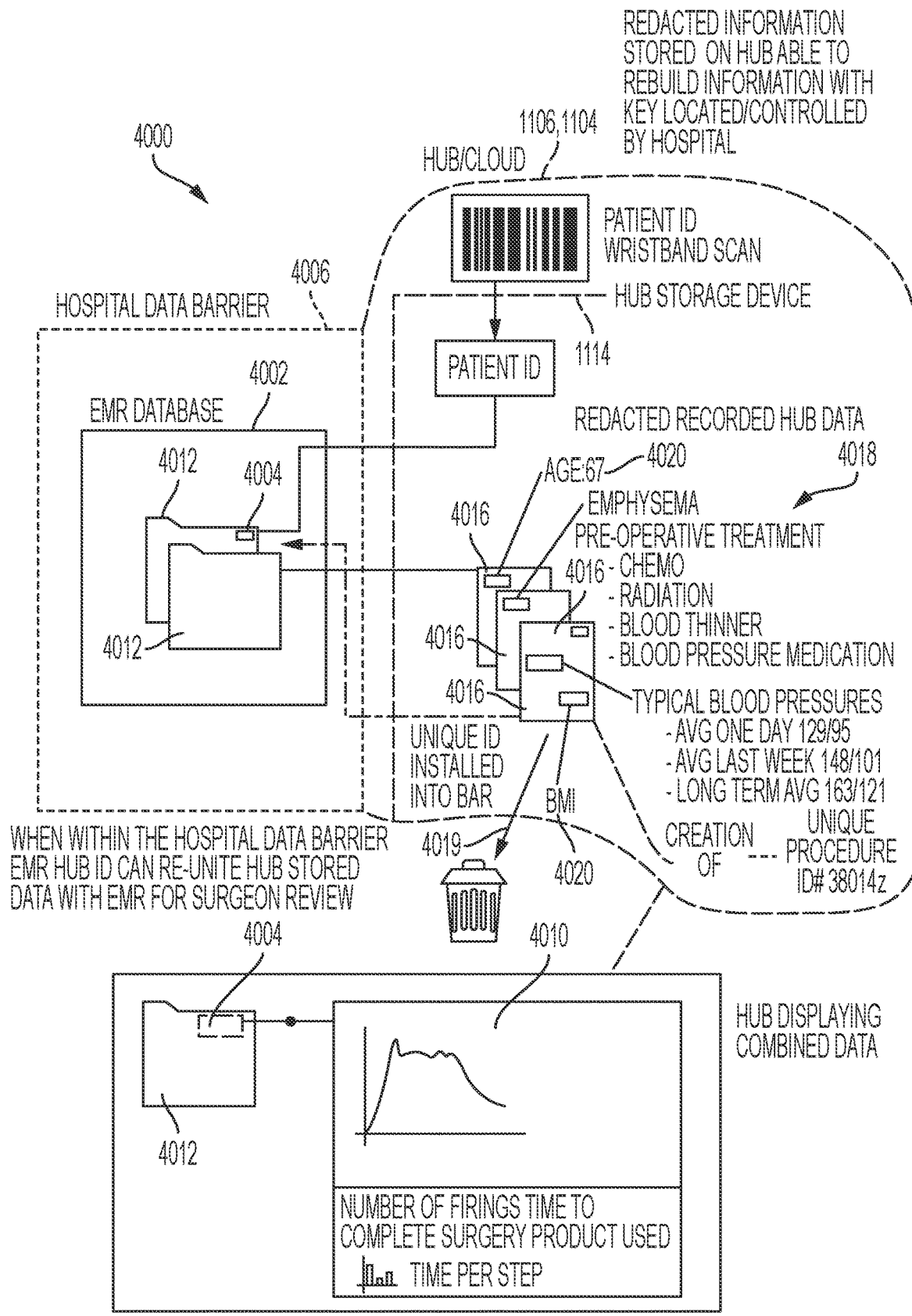
FIG. 11 is a diagram illustrating one embodiment of a technique for interacting with a patient Electronic Medical Record (EMR) database.

FIG. 11 illustrates a system 4000 and a technique for interacting with a patient EMR database 4002. A key 4004 can be embedded within the EMR database 4002 located within, e.g., a hospital or medical facility. A data barrier 4006 is provided to preserve patient data privacy and allows the reintegration of stripped and isolated data pairs, as described herein below, from the surgical hub 1106 or the cloud 1104 to be reassembled. The technique allows users full access to all the data collected during a surgical procedure, including the drug administration data, and patient information stored in the form of electronic medical records 4012. The reassembled data can be displayed on a monitor 4010 coupled to the surgical hub 1106 or secondary monitors but is not permanently stored on any surgical hub storage device 1114. The reassembled data is temporarily stored in a storage device 1114 located either in the surgical hub 1106 or the cloud 1104 and is deleted at the end of its use and overwritten to ensure it cannot be recovered. The key 4004 in the EMR database 4002 is used to reintegrate anonymized hub data back into full integrated patient electronic medical records 4012 data.

As shown in FIG. 11, the EMR database 4002 is located within the data barrier 4006. The EMR database 4002 can be configured to store, retrieve, and manage associative arrays, or other data structures known today as a "dictionary" or "hash." Dictionaries contain a collection of objects, or records, which in turn have many different fields within them, each containing data. The patient electronic medical records 4012 can be stored and retrieved using the key 4004 that uniquely identifies the patient electronic medical record 4012, and is used to quickly find the data within the EMR database 4002. The key-value EMR database 4002 system treats the data as a single opaque collection which can have different fields for every record.

Information from the EMR database 4002 can be transmitted to the surgical hub 1106 and the patient electronic medical records 4012. Data is redacted and stripped before it is sent to an analytics system based either on the hub 1106 or the cloud 1104. An anonymous data file 4016 is created by redacting personal patient data and stripping relevant patient data 4018 from the patient electronic medical record 4012. As used herein, the redaction process includes deleting or removing personal patient information from the patient electronic medical record 4012 to create a redacted record that includes only anonymous patient data. A redacted record is a record from which sensitive patient information has been expunged. Un-redacted data can be deleted 4019. The relevant patient data 4018 is also referred to herein as stripped/extracted data 4018. The stripped/extracted data 4018 is used by the surgical hub 1106 or cloud 1104 processing engines for analytic purposes and can be stored on the storage device 1114 of the surgical hub 1106 or can be stored on the cloud 1104 based analytics system storage device. Data stripping/extracting is described further in previously mentioned U.S. Pat. Pub. No. 2019/0200844 entitled "Method Of Hub Communication, Processing, Storage And Display" filed Dec. 4, 2018.

Figure 12:
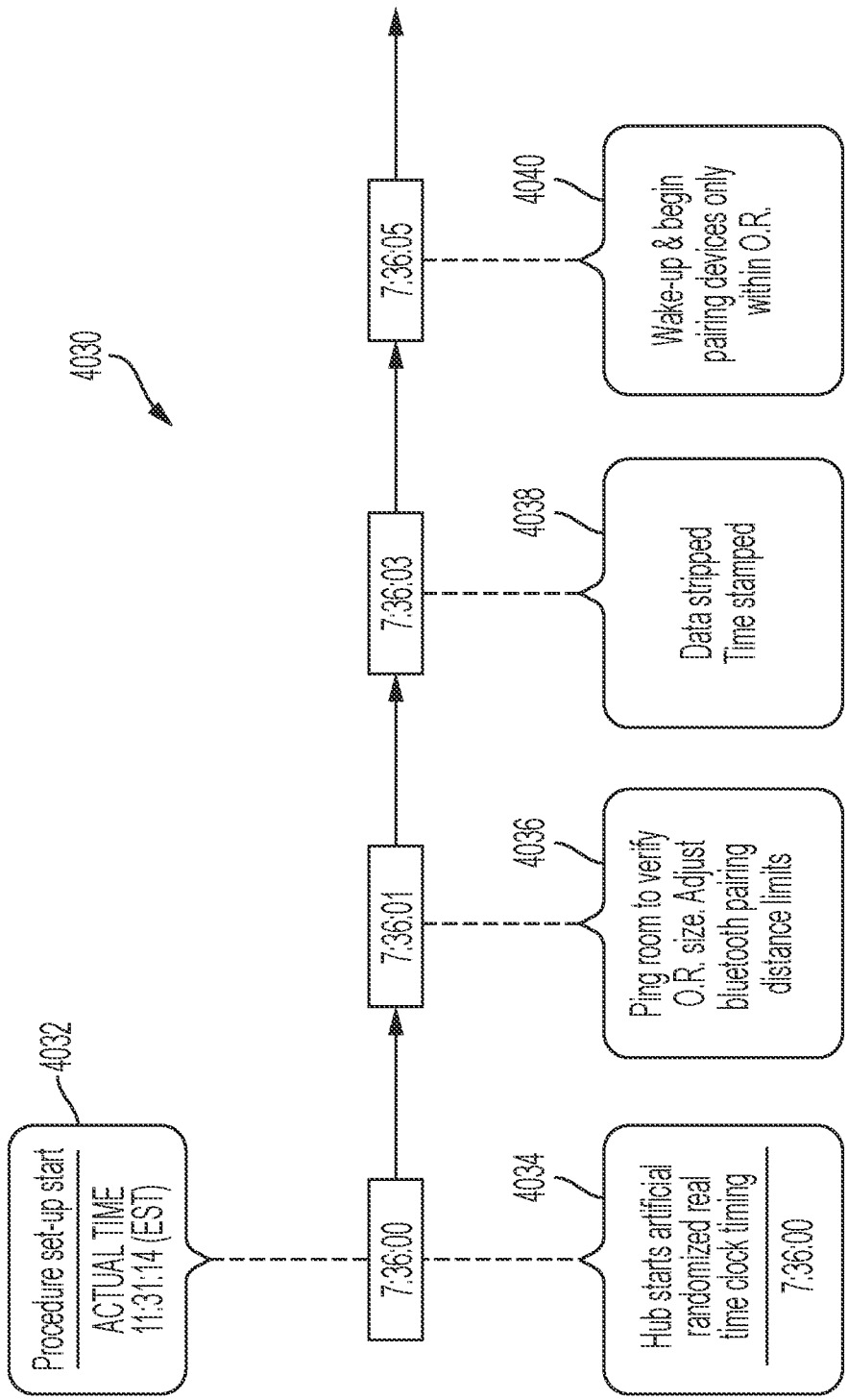
FIG. 12 is a diagram illustrating one embodiment of a process of anonymizing a surgical procedure by substituting an artificial time measure for a real time clock for all information stored internally within the instrument, robot, surgical hub, and/or hospital computer equipment.

The surgical hub anonymous data file 4016 can be rebuilt using a key 4004 stored in the EMR database 4002 to reintegrate the surgical hub anonymous data file 4016 back into a fully integrated patient electronic medical record 4012. The relevant patient data 4018 that is used in analytic processes can include information such as the patient's diagnoses of disease(s) (emphysema in this illustrated example), pre-operative treatment (e.g., chemotherapy, radiation, blood thinner, blood pressure medication, etc.), typical blood pressures, or any data that alone cannot be used to ascertain the identity of the patient. Data 4020 to be redacted includes personal information removed from the patient electronic medical record 4012, can include age, employer, body mass index (BMI), or any data that can be used to ascertain the identity of the patient. The surgical hub 1106 creates a unique anonymous procedure ID number (380$i$4$z$ in this illustrated example), for example, as described in FIG. 12. Within the EMR database 4002 located in the data barrier 4006, the surgical hub 1106 can reunite the data in the anonymous data file 4016 stored on the surgical hub 1106 storage device 1114 with the data in the patient electronic medical record 4012 stored on the EMR database 4002 for surgeon (or other user) review. The surgical hub 1106 displays the combined patient electronic medical record 4012 on a display or monitor 4010 coupled to the surgical hub 206. Ultimately, un-redacted data is deleted 4019 from the surgical hub 1106 storage 1114.

In some instances, a drug administration device being used in a surgical performance may experience a failure event. For instances where a failure event is detected and/or identified, communication methods can be utilized to isolate surgical data which is associated with the failure event (e.g., failure event surgical data) from surgical data which is not associated with the failure event (e.g., non-failure event surgical data) and communicate the surgical data which is associated with the failure event (e.g., failure event data) from the surgical hub 1106 to the cloud 1104 on a prioritized basis for analysis. In at least some embodiments, failure event surgical data is communicated from the surgical hub 1106 to the cloud 1104 on a prioritized basis relative to non-failure event surgical data.

Figure 13:
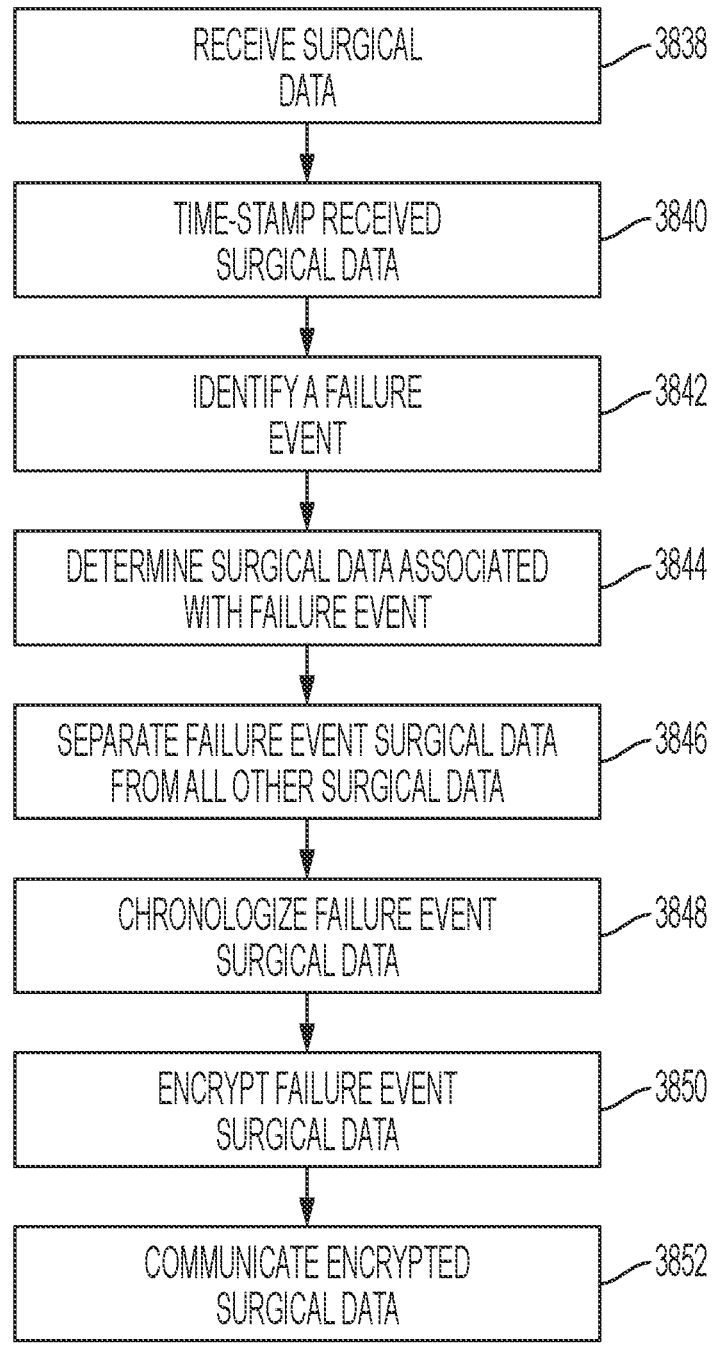
FIG. 13 is a flowchart illustrating one embodiment of a method of identifying surgical data associated with a failure event and communicating the identified surgical data to a cloud-based system on a prioritized basis.

FIG. 13 illustrates an embodiment of a system-implemented method of identifying surgical data associated with a failure event (e.g., failure event surgical data) and communicating the identified surgical data to a cloud-based system 205 on a prioritized basis. The method includes receiving 3838 surgical data at the surgical hub 1106. The surgical data is associated with a surgical procedure being performed on a patient. In an exemplary embodiment, the surgical data includes data received at the surgical hub 1106 from a drug administration device. The method also includes time-stamping 3840 the surgical data, identifying 3842 a failure event associated with the surgical procedure based on the surgical data, determining 3844 which of the surgical data is associated with the failure event (e.g., failure event surgical data), separating 3846 the surgical data associated with the failure event from all other surgical data (e.g., non-failure event surgical data) received at the surgical hub 1106, chronologizing 3848 the surgical data associated with the failure event, encrypting 3850 the surgical data associated with the failure event, and communicating 3852 the encrypted surgical data to the cloud 1104 on a prioritized basis.

More specifically, various surgical data can be captured during a surgical procedure, as discussed above. The captured surgical data, as well as other surgical data associated with the surgical procedure, can be communicated to the surgical hub 1106. The surgical data can include, for example, data associated with a drug delivery device utilized during the surgery, a surgical instrument utilized during the surgery, data associated with the patient, data associated with the facility where the surgical procedure was performed, and data associated with the surgeon and/or other medical personal who performed the surgical procedure. Either prior to or subsequent to the surgical data being communicated to and received by the surgical hub 1106, the surgical data can be time-stamped and/or stripped of all information which could identify the specific surgery, the patient, or the surgeon (and/or other medical personnel), so that the information is essentially anonymized for further processing and analysis by the cloud 1104.

Once a failure event has been detected and/or identified (e.g., which can be either during or after the surgical procedure), the surgical hub 1106 can determine which of the surgical data is associated with the failure event (e.g., failure event surgical data) and which of the surgical data is not associated with the surgical event (e.g., non-failure event surgical data). A failure event can include a failure event associated with a drug administration device, for example, a dispensing mechanism of the drug administration device not operating properly, a needle of the drug administration device not advancing properly, a needle of a drug administration device not retracting properly, an amount of drug delivered from the drug administration device not equaling a predetermined dosage amount, etc. For example, in a surgical procedure, an endoscope and/or other image capturing device can take snapshots while a drug administration device is actuated to deliver a drug therefrom. An imaging module of the hub 1106 can be configured to compare the snapshots to stored images and/or images downloaded from the cloud 1104 to detect a failure event, e.g., an image of an improperly advanced or retracted needle, an image of an malfunctioning dispensing mechanism, etc. Additionally or alternatively, the imaging module of the hub 1106 can be configured to analyze the snapshots themselves to detect a failure event. Additionally or alternatively, the surgical hub 1106 can be configured to communicate the snapshots to the cloud 1104, and a component of the cloud 1104 can be configured to perform the various imaging module functions described above to detect a failure event and to report the detection to the surgical hub 1106. For another example, a failure event can include a detection of a delivered drug dosage amount which is above or below the expected dosage amount. The drug administration device can include a sensor configured to monitor drug volume in the drug administration device's drug holder. The hub 1106 (and/or the cloud 1104) can be configured to receive monitored drug volume data from the sensor and be configured to compare the sensed drug volume to a stored drug volume, e.g., a starting drug volume or a previously sensed drug volume, to determine whether the expected dosage amount was delivered from the drug holder.

In response to the detected and/or identified failure event, the surgical hub 1106 can download a program from the cloud 1104 for execution by the drug administration device that experienced the failure event to correct the detected issue. The program can alters drug delivery device control parameters to, e.g., adjust needle advancement and/or retraction speed, cause another drug delivery to account for a too-low dosage amount, etc.

A failure event can be deemed to cover a certain time period, and all surgical data associated with that certain time period can be deemed to be associated with the failure event.

After the surgical data associated with the failure event has been identified, the identified surgical data (e.g., failure event surgical data) can be separated or isolated from all of the other surgical data associated with the surgical procedure (e.g., non-failure event surgical data). The separation can be realized, for example, by tagging or flagging the identified surgical data, by storing the identified surgical data apart from all of the other surgical data associated with the surgical procedure, or by storing only the other surgical data while continuing to process the identified surgical data for subsequent prioritized communication to the cloud 1104. The tagging or flagging of the identified surgical data can occur during the communication process when a datagram is generated as described in more detail below.

The time-stamping of all of the surgical data (e.g., either before or after the surgical data from the drug administration device is received at the surgical hub 1106) can be utilized by a component of the surgical hub 1106 to chronologize the identified surgical data associated with the failure event. The component of the surgical hub 1106 which utilizes the time-stamping to chronologize the identified surgical data can be, for example, the hub's processor. By chronologizing the identified surgical data, the cloud 1104 and/or other interested parties can receive data from the hub 1106 and subsequently better understand the conditions which were present leading up to the occurrence of the failure event and possibly pinpoint the exact cause of the failure event, thereby providing the knowledge to potentially mitigate a similar failure event from occurring during a similar surgical procedure performed at a future date.

Once the identified surgical data has been chronologized, the chronologized surgical data can be encrypted. Thus, the identified surgical data can be encrypted to help ensure the confidentiality of the identified surgical data, either while it is being stored at the surgical hub 1106 or while it is being transmitted to the cloud 1104 using the Internet or other computer networks. A component of the surgical hub 1106 can utilizes an encryption algorithm to convert the identified surgical data from a readable version to an encoded version, thereby forming the encrypted surgical data associated with the failure event. The component of the surgical hub which utilizes the encryption algorithm can be, for example, the hub's processor. Any of a variety of encryption techniques can be used, as will be appreciated by a person skilled in the art. The utilized encryption algorithm can be a symmetric encryption algorithm or an asymmetric encryption algorithm. Various encryption techniques for surgical data are further described in previously mentioned U.S. Pat. Pub. No. 2019/0200844 entitled "Method Of Hub Communication, Processing, Storage And Display" filed Dec. 4, 2018.

Figure 14:
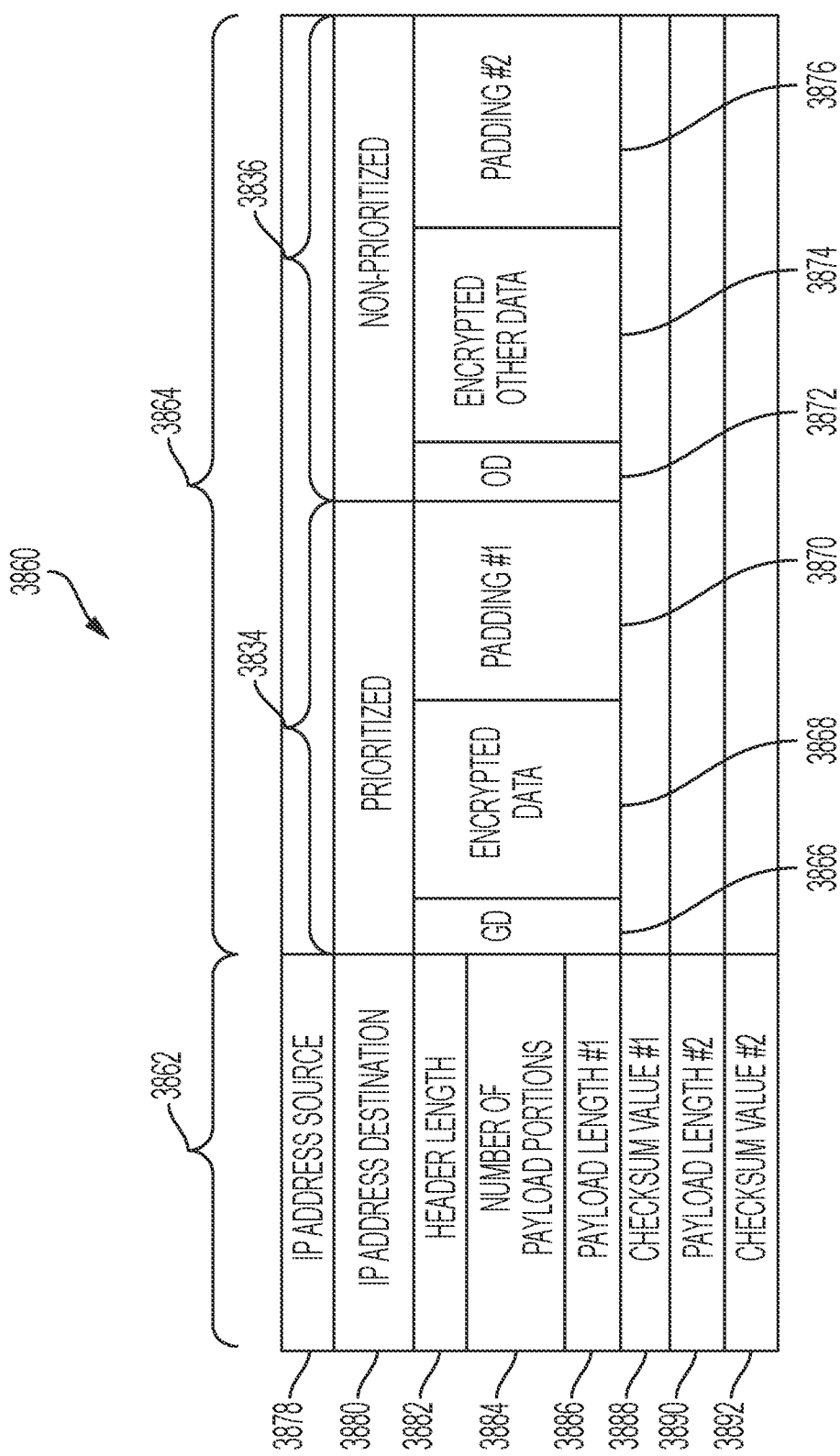
FIG. 14 is a schematic of one embodiment of a datagram.

After the identified surgical data has been encrypted, a component of the surgical hub 1106, e.g., the communications interface thereof, can communicate the encrypted surgical data associated with the failure event (e.g., encrypted failure event surgical data) to the cloud 1104, e.g., to a communications interface thereof. The communication of the encrypted surgical data (e.g., encrypted failure event surgical data) through the Internet can follow an IP which defines datagrams that encapsulate the encrypted surgical data to be delivered and which defines addressing methods that are used to label the datagram with source and destination information. A header or a payload of the datagram can include a field which includes a flag or a tag which identifies the encrypted surgical data (e.g., encrypted failure event surgical data) as being prioritized relative to other non-prioritized surgical data (e.g., encrypted non-failure event surgical data). One embodiment of such a datagram is shown in FIG. 14, where the payload 3864 of the datagram 3860 includes a field which indicates (e.g., a prioritized designation 3834) that the payload 3864 includes prioritized surgical data (e.g., combination data 3868). According to various aspects, the payload 3864 of the datagram 3860 can also include non-flagged/non-tagged/non-prioritized surgical data 3836 (e.g., other surgical data 3874) as shown in FIG. 14.

Prior to the identified surgical data (e.g., failure event surgical data) being encrypted, the identified surgical data can be compressed (if not already compressed by the source(s) of the relevant surgical data). The compression allows for a smaller representation of the surgical data associated with the failure event to be subsequently encrypted and communicated to the cloud 1104. For the compression, a component of the surgical hub 1106, e.g., a processor thereof, can utilize a compression algorithm to convert a representation of the identified surgical data to a smaller representation of the identified surgical data, thereby allowing for a more efficient and economical encryption of the identified surgical data (less data to encrypt utilizes less processing resources) and a more efficient and economical communication of the encrypted surgical data (smaller representations of the surgical data within the payload of the datagrams allow for more identified surgical data to be included in a given datagram, for more identified surgical data to be communicated within a given time period, and/or for identified surgical data to be communicated with fewer communication resources). The utilized compression algorithm can be a lossless compression algorithm or a lossy compression algorithm.

In instances where other non-prioritized surgical data (e.g., non-failure event surgical data) is to be communicated with prioritized surgical data (e.g., failure event surgical data), the other non-prioritized surgical data can be time-stamped, compressed, and/or encrypted in a manner identical to or different from that described above regarding the surgical data identified as associated with a failure event (e.g., failure event surgical data), and the surgical hub 1106 can be programmed/configured to generate a datagram which includes both the encrypted prioritized surgical data (e.g., encrypted failure event surgical data) and the encrypted other non-prioritized surgical data (e.g., encrypted non-failure event surgical data). For example, in light of FIG. 14, the payload 3864 of the datagram 3860 can be divided into two or more distinct payload data portions (e.g., one for the prioritized surgical data 3834, one for the non-prioritized surgical data 3836), with each portion having an identifying bit (e.g., device data (GD) 3866, other data (OD) 3872), the associated encrypted data (e.g., encrypted prioritized surgical data 3868, encrypted non-prioritized surgical data 3874), and the associated padding 3870, 3876, if needed, respectively. Further, the header 3862 can include IP address source 3878, IP address destination 3880, and header length 3882. For example, the header 3862 can include a field designating the number of payload data portions 3884 included in the payload 3864 of the datagram 3860. The header 3862 can include fields designating the payload length 3886, 3890 and the checksum value 3888, 2892 for each payload data portion 3834, 3836, respectively. Although only two payload data portions are shown in FIG. 14, it will be appreciated by a person skilled in the art that the payload 3864 of the datagram 3860 can include any quantity/number of payload data portions (e.g., one, two, three, four, five, etc.), where each payload data portion includes data associated with a different aspect of the surgical procedure. The datagram 3860 can then be communicated from the surgical hub 1106 through the Internet (or other means) to the cloud 1104 following an IP which: (1) defines datagrams that encapsulate the encrypted data and the encrypted stripped/other data to be delivered, and (2) defines addressing methods that are used to label the datagram with source and destination information.

Once a failure event associated with a drug administration device has been identified, the surgical hub 1106 and/or the cloud 1104 can subsequently flag or tag the drug administration device which was utilized during the surgical procedure for inoperability and/or removal. For example, information (e.g., serial number, ID) associated with the drug administration device and stored at the surgical hub 1106 and/or the cloud 1104 can be utilized to effectively block the drug administration device from being used again (e.g., blacklisted) in the same surgical procedure or subsequently. For another example, information (e.g., serial number, ID, etc.) associated with the drug administration device can initiate the printing of a shipping slip and shipping instructions for returning the drug administration device back to a manufacturer or other designated party so that a thorough analysis/inspection of the drug administration device can be performed (e.g., to determine the cause of the failure). Once the cause of a failure is determined (e.g., via the surgical hub 1106 and/or the cloud 1104), the surgical hub 1106 can download a program from the cloud 1104 for execution by the drug administration device, e.g., by a processor thereof, that corrects the determined cause of the failure (i.e., program that alters drug administration device's control parameters to prevent the failure from occurring again).

The surgical hub 1106 and/or the cloud 1106 can provide, e.g., display (e.g., via hub display and/or drug administration device user interface) and/or sound (e.g., via hub speaker and/or drug administration device indicator), a reminder to administrators, staff, and/or other personnel to physically remove the drug administration device that experienced a failure event from the operating room (e.g., if detected as still present in the operating room) and/or to send the drug administration device that experienced the failure event to the manufacturer or other designated party. The reminder can be set up to be provided/displayed periodically until an administrator or other user can remove the flag or tag of the drug administration device from the surgical hub 1106 and/or the cloud 1104. An administrator or other user can remove the flag or tag once the administrator or other user can confirm (e.g., system tracking of the drug administration device via its serial number/ID) that the drug administration device has been received by the manufacturer or other designated party.

By using the above-described method to flag and/or track surgical data associated with a failure event, a closed loop control of the surgical data associated with the failure event and/or with a drug administration device can be realized. Additionally, the surgical hub 206 can be utilized to effectively manage the utilization (or non-utilization) of drug administration devices which have or potentially could be utilized during a surgical procedure.

The surgical hub 1106 and/or cloud 1104 can be configured to control which components (e.g., surgical instrument, drug administration device, etc.) are being utilized in its interactive surgical system 1000 to perform surgical procedures (e.g., to minimize future failure events, to avoid the use of unauthorized or knock-off components). As such, since an interactive surgical system 1000 (using the example of FIG. 9) can include a plurality of surgical hubs 1006, a cloud 1004 and/or each surgical hub 1006 of the interactive surgical system 1000 may want to track component-surgical hub combinations utilized over time. In one aspect, upon/after a component is connected to/used with a particular surgical hub 1006 (e.g., a drug administration device wired/wirelessly connected to the particular surgical hub 1006, a surgical instrument wired/wirelessly connected to the particular surgical hub 1006, an energy device connected to the particular surgical hub 1006 via a generator module, etc.), the particular surgical hub 1006 can communicate a record/block of that connection/use (e.g., linking respective unique identifiers of the connected devices) to the cloud 1004 and/or to the other surgical hubs 1006 in the interactive surgical system 100. For example, upon/after the connection/use of a drug administration device, a particular surgical hub 1006 may communicate a record/block (e.g., linking a unique identifier of the drug administration device to a unique identifier of the particular surgical hub 1006) to the cloud 1004 and/or other surgical hubs 1006 in the interactive surgical system 100. If this is the first time the component is connected to/used with a surgical hub 1006 in the interactive surgical system 100, the cloud 1004 and/or each surgical hub 1006 of the interactive surgical system 1000 can store the record/block as a genesis record/block. The genesis record/ block stored at the cloud 1004 and/or each surgical hub 1006 can include a time stamp. However, if this is not the first time the component has been connected to/used with a surgical hub 1006 in the interactive surgical system 100, the cloud 1004 and/or each surgical hub 1006 of the interactive surgical system 1000 can store the record/block as a new record/block in a chain of record/blocks associated with the component. The new record/block can include a cryptographic hash of the most recently communicated record/block stored at the cloud 1004 and/or each surgical hub 1006, the communicated linkage data, and a time stamp. Each cryptographic hash links each new record/block (e.g., each use of the component) to its prior record/block to form a chain confirming the integrity of each prior record/block(s) back to an original genesis record/block (e.g., first use of the component). This blockchain of records/blocks can be developed at the cloud 1004 and/or each surgical hub 1006 of the interactive surgical system 1000 to permanently and verifiably tie usage of a particular component to one or more than one surgical hub 1006 in the interactive surgical system 1000 over time. This approach may be similarly applied to sub-components (e.g., dispensing mechanism, drug holder, drug, discharge nozzle, housing, energy source, dispensing mechanism protection mechanism, trigger, infusion line, pump, power supply, valve, metering mechanism, etc. of a drug administration device) of a component when/after the component is connected to/used with a particular surgical hub 1006 of an interactive surgical system 100.

The cloud 1004 and/or each surgical hub 1006 can utilize such records/blocks to trace usage of a particular component and/or a sub-component back to its initial usage in the interactive surgical system 100. For example, if a particular component (e.g., a drug administration device, a surgical instrument, etc.) and/or a particular sub-component is flagged/tagged as related to a failure event, the cloud 1004 and/or a surgical hub 1006 can analyze such records/blocks to determine whether past usage of that component and/or sub-component contributed to or caused the failure event (e.g., overused, previously detected failure event, etc.). In one example, the cloud 1004 may determine that a sub-component of a component may actually be contributing/causing the failure event and then tag/flag that component for inoperability and/or removal based on the determination.

According to another aspect, the cloud 1004 and/or the surgical hub 1006 can control which components (e.g., drug administration device, surgical instrument, energy device, etc.) are being utilized in the interactive surgical system 1000 to perform surgical procedures by authenticating the component and/or its supplier/manufacturer. The supplier/manufacturer of a component can associate a serial number and a source ID with the component. The supplier/manufacturer can create/generate a private key for the serial number, encrypt the serial number with the private key, and store the encrypted serial number and the source ID on an electronic chip (e.g., memory) in the component prior to shipment to a surgical site. Here, upon/after connection of the component to the surgical hub 1006, the surgical hub 1006 can read the encrypted serial number and the source ID from the electronic chip. In response, the surgical hub 1006 can send a message including the encrypted serial number to a server of the supplier/manufacturer associated with the source ID (e.g., directly or via the cloud 1004). The surgical hub 206 can encrypt the message using a public key associated with that supplier/manufacturer. In response, the surgical hub 1006 can receive a message including the private key the supplier/manufacturer generated for/associated with that encrypted serial number from the supplier/manufacturer server (e.g., directly or via the cloud 1004). The supplier/manufacturer server can encrypt the message using a public key associated with the surgical hub 1006. Further, the surgical hub 1006 may can decrypt the message (e.g., using a private key paired to the public key used to encrypt the message) to reveal the private key associated with the encrypted serial number. The surgical hub 1006 can then decrypt the encrypted serial number, using that private key, to reveal the serial number. Further, the surgical hub 1006 can then compare the decrypted serial number to a comprehensive list of authorized serial numbers (e.g., stored at the surgical hub 1006 and/or the cloud 1004 and/or downloaded to the hub 1006 from the cloud 1004, e.g., received separately from the supplier/manufacturer) and permit use of the connected component if the decrypted serial number matches an authorized serial number. Initially, such a process permits the surgical hub 1006 to authenticate the supplier/manufacturer. In particular, the surgical hub 1006 encrypted the message including the encrypted serial number using a public key associated with the supplier/manufacturer. As such, receiving a response message (i.e., comprising the private key) authenticates the supplier/manufacturer to the surgical hub 1006 (i.e., otherwise the supplier/manufacturer would not have access to the private key paired to the public key used by the surgical hub 1006 to encrypt the message, and the supplier/manufacturer would not have been able to associate the encrypted serial number received in the message to its already generated private key). Furthermore, such a process permits the surgical hub 1006 to authenticate the connected component itself. In particular, the supplier/manufacturer (e.g., just authenticated) encrypted the serial number of the component using the delivered private key. Upon secure receipt of the private key, the surgical hub 1006 is able to decrypt the encrypted serial number (e.g., read from the connected component), which authenticates the component and/or its association with the supplier/manufacturer (e.g., only that private key as received from that supplier/manufacturer would decrypt the encrypted serial number). Nonetheless, the surgical hub 1006 further verifies the component as authentic (e.g., compares the decrypted serial number to a comprehensive list of authorized serial numbers received separately from the supplier/manufacturer). Such aspects as described above can alternatively be performed by the cloud 1004 and/or a combination of the cloud 1004 and the surgical hub 1006 to control which components (e.g., drug administration device, surgical device/instrument, energy device, etc.) are being utilized in the interactive surgical system 1000 (e.g., to perform surgical procedures) by authenticating the component and/or its supplier/manufacturer. Such described approaches may prevent the use of knock-off component(s) within the interactive surgical system 1000 and ensure the safety and well-being of surgical patients.

The electronics of a component (e.g., drug administration device, surgical device/instrument, energy device, etc.) can store (e.g., in memory) data associated with usage of that component (e.g., usage data for a drug administration device such as number of drug doses delivered, number of drug doses remaining, drug delivery algorithms executed, designation as a single-use component, etc.). The surgical hub 1006 and/or the cloud 1004, upon/after connection of the component to the interactive surgical system 100, can read such usage data from the memory of a component and write back at least a portion of that usage data for storage (e.g., in memory) at the surgical hub 1006 and/or for storage at the cloud 1004 (e.g., individually and/or under a blockchain approach discussed herein). The surgical hub 1006 and/or the cloud 1004, upon/after a subsequent connection of that component to the interactive surgical system, can again read such usage data and compare that usage to previously stored usage data. Here, if a discrepancy exists, if a predetermined/ authorized usage has been met, or if the component is no longer usable (e.g., no drug doses remaining for delivery from a drug delivery device, if a minimum number of drug doses is needed from a drug delivery device during a surgical procedure but less than the minimum number of drug doses remains in the drug delivery device, etc.) the surgical hub 1006 and/or the cloud 1004 prevent use of that component (e.g., blacklisted, rendered inoperable, flagged for removal, etc.) on the interactive surgical system 100. Such an approach prevents bypass of the encryption chip systems. If the component's electronics has been tampered with (e.g., memory reset, number of uses altered, firing algorithms altered, single-use device designated as a multi-use device, etc.), a discrepancy will exist, and the component's use will be controlled/prevented.

Data received at the cloud 1004 from the hub 1006, such as data received at the hub 1006 from a drug administration device and data received at the hub 1006 from a surgical instrument, can be sorted and prioritized at the cloud 1004 based on criticality (e.g., the severity of a medical event and/or failure event associated with the data, unexpectedness, suspiciousness, etc.). This sorting and prioritization can be used in conjunction with other cloud 1004 functions to improve cloud-based analytics and operations. For example, a data sorting and prioritization module at the cloud 1004 can assign a priority to the data analysis performed by a data collection and aggregation module of the cloud 1004 and patient outcome analysis modules of the cloud 1004. Different prioritization levels can result in particular responses from the cloud 1004 (corresponding to a level of urgency) such as escalation for an expedited response, special processing, exclusion from aggregated medical data databases at the cloud 1004, or other suitable responses. Moreover, if necessary, the cloud 1004 can transmit a request (e.g., a push message) through the hub 1006 for additional data from corresponding components, e.g., corresponding drug administration devices or surgical instruments. The push message can result in a notification displayed on the corresponding hub 1006 for requesting supporting or additional data. This push message can be required in situations in which the cloud 1004 detects a significant irregularity or outlier and the cloud 1004 cannot determine the cause of the irregularity. The server 1013 of the cloud 1004 can be programmed to trigger this push message in certain significant circumstances, such as when data is determined to be different from an expected value beyond a predetermined threshold or when it appears security has been comprised, for example. Cloud-based data sorting, prioritizing, and analyzing is further described in previously mentioned U.S. Pat. Pub. No. 2019/0207857 entitled "Surgical Network Determination Of Prioritization Of Communication, Interaction, Or Processing Based On System Or Device Needs" filed Nov. 6, 2018 and U.S. Pat. Pub. No. 2019/006555 entitled "Cloud-based Medical Analytics For Customization And Recommendations To A User" filed Mar. 29, 2018.

Devices and systems disclosed herein can be designed to be disposed of after a single use, or they can be designed to be used multiple times. In either case, however, the devices can be reconditioned for reuse after at least one use. Reconditioning can include any combination of the steps of disassembly of the devices, followed by cleaning or replacement of particular pieces, and subsequent reassembly. In particular, the devices can be disassembled, and any number of the particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

It can be preferred that devices disclosed herein be sterilized before use. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 issued Feb. 14, 2012 and entitled "System And Method Of Sterilizing An Implantable Medical Device." It is preferred that device, if implanted, is hermetically sealed. This can be done by any number of ways known to those skilled in the art.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical system, comprising:
a drug administration device configured to administer a drug to a patient during performance of a surgical procedure, the drug administration device including a first communications interface and a first processor configured to cause the first communications interface to transmit data regarding operation of the drug administration device during the performance of the surgical procedure;
a first surgical hub including a second processor and a second communications interface, the second communications interface being configured to receive the transmitted data from the first communications interface during the performance of the surgical procedure;
a cloud-based server configured to be remotely located from the drug administration device and from the first surgical hub, the server including a third communications interface configured to receive data from the second communications interface that the first surgical hub received from the drug administration device regarding the operation of the drug administration device during the performance of the surgical procedure;
a second drug administration device configured to administer a drug to a second patient during performance of a second surgical procedure, the second drug administration device including a fourth communications interface; and
a second surgical hub including a second processor and a fifth communications interface, the fifth communications interface being configured to receive data from the fourth communications interface during the performance of the second surgical procedure;
wherein the third communications interface is configured to receive data from the fifth communications interface;

wherein the cloud-based server is configured to be remotely located from the second drug administration device and from the second surgical hub; and wherein the drug administration device and the first surgical hub are configured to be remotely located from the second drug administration device and from the second surgical hub.

2. The system of claim 1, wherein the data regarding operation of the drug administration device during the performance of the surgical procedure includes at least one of:

image data showing at least a portion of the drug administration device during the performance of the surgical procedure, and data gathered by a sensor of the drug administration device during the performance of the surgical procedure.

3. The system of claim 2, wherein the data regarding operation of the drug administration device during the performance of the surgical procedure includes at least the image data;

a memory of the first surgical hub is configured to store second image data conveying correct administration of the drug administration device; and the second processor is configured to determine, using the image data and the second image data, whether the drug administration device experienced a failure event during the performance of the surgical procedure.

4. The system of claim 2, wherein the data regarding operation of the drug administration device during the performance of the surgical procedure includes at least the data gathered by the sensor; and the second processor is configured to determine, using the data gathered by the sensor, whether the drug administration device experienced a failure event during the performance of the surgical procedure.

5. The system of claim 1, wherein the second processor is configured to determine, using the received data, whether the drug administration device experienced a failure event during the performance of the surgical procedure.

6. The system of claim 5, wherein, in response to determining that the drug administration device experienced a failure event during the performance of the surgical procedure, the second processor is configured to cause the second communications interface to transmit an operation instruction to the first communications interface of the drug administration device that instructs the drug administration device to alter its operation.

7. The system of claim 1, wherein the cloud-based server includes a third processor configured to cause an electronic medical record (EMR) of the patient to be updated based on the data received from the first surgical hub.

8. The system of claim 7, wherein the third processor is configured to, based on the data from the first surgical hub and on the EMR of the patient, cause the third communications interface to transmit an alert to the second communications interface of the first surgical hub that indicates a critical condition related to the drug.

9. The system of claim 1, wherein the second communications interface of the first surgical hub is configured to receive image data from the third communications interface of the cloud-based server, the image data conveying correct administration of the drug administration device; and the second processor of the first surgical hub is configured to determine, using the image data and the data that the first surgical hub received from the drug administration device, whether the drug administration device experienced a failure event during the performance of the surgical procedure.

10. The system of claim 1, wherein the cloud-based server includes a memory storing conveying correct administration of the drug administration device, and the cloud-based server includes a third processor configured to determine, using the image data and the data that the cloud-based server received from the first surgical hub, whether the drug administration device experienced a failure event during the performance of the surgical procedure.

11. The system of claim 1, wherein the second communications interface of the first surgical hub is configured to communicate an operation instruction to the first communications interface of the drug administration device that instructs the drug administration device to alter its operation, the operation instruction being based on the data the first surgical hub received from the drug administration device.

12. The system of claim 1, wherein the drug administration device and the first surgical hub are each configured to be located in an operating room in which the surgical procedure is being performed.

13. A surgical method, comprising:

administering the drug to the patient from the drug administration device of claim 1 during the performance of the surgical procedure;

after the administration of the drug, causing the first communications interface to transmit data to the second communications interface of claim 1 regarding operation of the drug administration device during the performance of the surgical procedure.

14. The method of claim 13, further comprising the second processor determining, using the received data, whether the drug administration device experienced a failure event during the performance of the surgical procedure.

15. The method of claim 14, further comprising, in response to determining that the drug administration device experienced a failure event during the performance of the surgical procedure, the second processor causing the second communications interface to transmit an operation instruction to the first communications interface of the drug administration device that instructs the drug administration device to alter its operation.

16. The method of claim 13, further comprising the second processor causing a display of the first surgical hub to show information indicative of the received data.

17. The method of claim 13, further comprising the second processor causing the second communications interface to communicate the received data to a cloud-based server.

18. The method of claim 17, further comprising the second processor prioritizing the received data before causing the second communications interface to communicate the received data to the cloud-based server.

19. A surgical system, comprising:

a drug administration device configured to administer a drug to a patient during performance of a surgical procedure, the drug administration device including a first communications interface and a first processor configured to cause the first communications interface to transmit data regarding operation of the drug administration device during the performance of the surgical procedure;

a surgical hub including a second processor and a second communications interface, the second communications interface being configured to receive the transmitted data from the first communications interface during the performance of the surgical procedure; and a cloud-based server configured to be remotely located from the drug administration device and from the surgical hub, the server including a third communications interface configured to receive data from the second communications interface that the surgical hub received from the drug administration device regarding the operation of the drug administration device during the performance of the surgical procedure;

wherein the cloud-based server includes a third processor configured to cause an electronic medical record (EMR) of the patient to be updated based on the data received from the surgical hub; and wherein the third processor is configured to, based on the data from the surgical hub and on the EMR of the patient, cause the third communications interface to transmit an alert to the second communications interface of the surgical hub that indicates a critical condition related to the drug.

20. A surgical system, comprising:

a drug administration device configured to administer a drug to a patient during performance of a surgical procedure, the drug administration device including a first communications interface and a first processor configured to cause the first communications interface to transmit data regarding operation of the drug administration device during the performance of the surgical procedure;

a surgical hub including a second processor and a second communications interface, the second communications interface being configured to receive the transmitted data from the first communications interface during the performance of the surgical procedure; and a cloud-based server configured to be remotely located from the drug administration device and from the surgical hub, the server including a third communications interface configured to receive data from the second communications interface that the surgical hub received from the drug administration device regarding the operation of the drug administration device during the performance of the surgical procedure;

wherein the second communications interface of the surgical hub is configured to receive image data from the third communications interface of the cloud-based server, the image data conveying correct administration of the drug administration device; and the second processor of the surgical hub is configured to determine, using the image data and the data that the surgical hub received from the drug administration device, whether the drug administration device experienced a failure event during the performance of the surgical procedure.

21. A surgical system, comprising:

a drug administration device configured to administer a drug to a patient during performance of a surgical procedure, the drug administration device including a first communications interface and a first processor configured to cause the first communications interface to transmit data regarding operation of the drug administration device during the performance of the surgical procedure;

a surgical hub including a second processor and a second communications interface, the second communications interface being configured to receive the transmitted data from the first communications interface during the performance of the surgical procedure; and a cloud-based server configured to be remotely located from the drug administration device and from the surgical hub, the server including a third communications interface configured to receive data from the second communications interface that the surgical hub received from the drug administration device regarding the operation of the drug administration device during the performance of the surgical procedure;

wherein the cloud-based server includes a memory storing conveying correct administration of the drug administration device, and the cloud-based server includes a third processor configured to determine, using the image data and the data that the cloud-based server received from the surgical hub, whether the drug administration device experienced a failure event during the performance of the surgical procedure.

* * * * *